US011191556B2

(12) United States Patent
Jalgaonkar et al.

(10) Patent No.: US 11,191,556 B2
(45) Date of Patent: Dec. 7, 2021

(54) CATHETER INCLUDING AN EXPANDABLE MEMBER

(71) Applicant: Covidien LP, Mansfield, MA (US)

(72) Inventors: Ujwal Jalgaonkar, Irvine, CA (US); Edwin Bon, Lake Elsinore, CA (US); Brian Roselauf, Rancho Santa Margarita, CA (US)

(73) Assignee: COVIDIEN LP, Mansfield, MA (US)

( * ) Notice: Subject to any disclaimer, the term of this patent is extended or adjusted under 35 U.S.C. 154(b) by 201 days.

(21) Appl. No.: 15/909,528

(22) Filed: Mar. 1, 2018

(65) Prior Publication Data

US 2019/0269491 A1 Sep. 5, 2019

(51) Int. Cl.
*A61B 17/221* (2006.01)
*A61M 25/00* (2006.01)
(Continued)

(52) U.S. Cl.
CPC ....... *A61B 17/221* (2013.01); *A61M 25/0067* (2013.01); *A61M 25/0074* (2013.01); *A61M 25/0082* (2013.01); *A61M 25/0102* (2013.01); *A61B 2017/2215* (2013.01); *A61B 2017/22035* (2013.01); *A61F 2/011* (2020.05); *A61F 2002/016* (2013.01); *A61M 25/00* (2013.01); *A61M 25/005* (2013.01); *A61M 25/0009* (2013.01); *A61M 25/0045* (2013.01); *A61M 25/0054* (2013.01); *A61M 2025/0024* (2013.01);
(Continued)

(58) Field of Classification Search
CPC .. A61F 2/013; A61F 2002/16; A61F 2002/18; A61F 2/011; A61F 2002/9528; A61B 2017/2215
See application file for complete search history.

(56) References Cited

U.S. PATENT DOCUMENTS

| 4,794,928 A | 1/1989 | Kletschka |
| 5,100,381 A * | 3/1992 | Burns ................. A61M 25/104 |
| | | 604/103 |

(Continued)

FOREIGN PATENT DOCUMENTS

| DE | 102007048794 A1 | 4/2009 |
| EP | 0810003 A2 | 12/1997 |

(Continued)

OTHER PUBLICATIONS

International Search Report and Written Opinion issued in International Application No. PCT/US2019/018993, dated Jun. 3, 2019, 15 pp.

(Continued)

*Primary Examiner* — Melanie R Tyson
*Assistant Examiner* — Mohammed S Adam
(74) *Attorney, Agent, or Firm* — Shumaker & Sieffert, P.A.

(57) ABSTRACT

In some examples, a catheter includes an elongated body including a proximal portion and a distal portion. The elongated body includes an inner liner, an outer jacket, a structural support member positioned between at least a portion of the inner liner and at least a portion of the outer jacket, and an expandable member coupled to the structural support member at the distal portion of the elongated body. The expandable member may be configured to expand radially outward, e.g., to engage a clot within vasculature of a patient.

30 Claims, 12 Drawing Sheets

(51) Int. Cl.
  *A61M 25/01* (2006.01)
  *A61B 17/22* (2006.01)
  *A61F 2/01* (2006.01)
(52) U.S. Cl.
  CPC .............. *A61M 2025/0047* (2013.01); *A61M 2025/018* (2013.01)

(56) References Cited

U.S. PATENT DOCUMENTS

| | | | |
|---|---|---|---|
| 5,312,356 A * | 5/1994 | Engelson | A61M 25/0052 604/164.13 |
| 5,653,684 A | 8/1997 | Laptewicz et al. | |
| 5,944,728 A * | 8/1999 | Bates | A61B 17/221 604/264 |
| 6,086,543 A * | 7/2000 | Anderson | A61B 10/0233 600/567 |
| 6,099,534 A * | 8/2000 | Bates | A61B 17/221 606/113 |
| 6,179,860 B1 * | 1/2001 | Fulton, III | A61M 25/04 606/116 |
| 6,183,482 B1 * | 2/2001 | Bates | A61B 17/221 606/113 |
| 6,224,612 B1 * | 5/2001 | Bates | A61B 17/221 606/114 |
| 6,290,710 B1 * | 9/2001 | Cryer | A61F 2/011 606/200 |
| 6,632,236 B2 | 10/2003 | Hogendijk | |
| 6,695,858 B1 | 2/2004 | Dubrul et al. | |
| 6,960,222 B2 * | 11/2005 | Vo | A61B 17/12 604/103.07 |
| 7,214,237 B2 * | 5/2007 | Don Michael | A61F 2/013 606/200 |
| 8,366,735 B2 | 2/2013 | Bose et al. | |
| 8,469,970 B2 | 6/2013 | Diamant et al. | |
| 8,535,293 B2 | 9/2013 | Faherty et al. | |
| 8,545,526 B2 | 10/2013 | Martin et al. | |
| 8,574,283 B1 * | 11/2013 | Kamat | A61F 2/954 623/1.11 |
| 8,795,305 B2 | 8/2014 | Martin et al. | |
| 9,427,252 B2 | 8/2016 | Sos | |
| 9,668,849 B2 | 6/2017 | Shimon | |
| 2002/0143362 A1 | 10/2002 | Macoviak et al. | |
| 2004/0210236 A1 * | 10/2004 | Allers | A61M 1/3621 606/108 |
| 2004/0260333 A1 * | 12/2004 | Dubrul | A61B 17/22 606/200 |
| 2005/0187570 A1 * | 8/2005 | Nguyen | A61B 17/221 606/159 |
| 2005/0228417 A1 * | 10/2005 | Teitelbaum | A61B 17/22031 606/159 |
| 2005/0288596 A1 * | 12/2005 | Eigler | A61B 5/0215 600/485 |
| 2006/0015136 A1 * | 1/2006 | Besselink | A61F 2/013 606/200 |
| 2006/0036218 A1 * | 2/2006 | Goodson, IV | A61M 25/0054 604/264 |
| 2007/0093781 A1 * | 4/2007 | Kugler | A61B 17/221 604/510 |
| 2008/0086110 A1 | 4/2008 | Galdonik et al. | |
| 2009/0005757 A1 * | 1/2009 | Taber | A61M 25/02 604/523 |
| 2009/0076539 A1 * | 3/2009 | Valaie | A61B 17/22031 606/200 |
| 2009/0112184 A1 * | 4/2009 | Fierens | A61B 17/12 604/509 |
| 2009/0292307 A1 * | 11/2009 | Razack | A61B 17/221 606/200 |
| 2010/0030256 A1 * | 2/2010 | Dubrul | A61B 10/0266 606/200 |
| 2011/0022149 A1 * | 1/2011 | Cox | A61B 17/12181 623/1.11 |
| 2012/0116351 A1 * | 5/2012 | Chomas | A61F 2/013 604/508 |
| 2013/0018318 A1 * | 1/2013 | Ravichandran | A61B 25/0012 604/172 |
| 2013/0226166 A1 * | 8/2013 | Chomas | A61B 18/1492 606/33 |
| 2013/0237919 A1 * | 9/2013 | Liungman | A61M 25/04 604/174 |
| 2013/0253474 A1 * | 9/2013 | Farhangnia | A61M 25/0071 604/510 |
| 2013/0253622 A1 * | 9/2013 | Hooven | A61B 18/1492 607/101 |
| 2013/0345739 A1 * | 12/2013 | Brady | A61B 17/221 606/200 |
| 2014/0074144 A1 * | 3/2014 | Shrivastava | A61M 39/06 606/200 |
| 2014/0155908 A1 * | 6/2014 | Rosenbluth | A61B 17/320725 606/127 |
| 2014/0243882 A1 * | 8/2014 | Ma | A61F 2/013 606/200 |
| 2014/0371779 A1 * | 12/2014 | Vale | A61B 17/12109 606/200 |
| 2015/0133990 A1 * | 5/2015 | Davidson | A61F 2/0105 606/200 |
| 2015/0272716 A1 * | 10/2015 | Pinchuk | A61F 2/013 606/200 |
| 2015/0313732 A1 * | 11/2015 | Fulton, III | A61B 17/22 623/1.11 |
| 2015/0343178 A1 * | 12/2015 | Fulton, III | A61M 25/0084 604/509 |
| 2015/0359549 A1 * | 12/2015 | Lenker | A61B 17/12118 600/585 |
| 2016/0000450 A1 * | 1/2016 | Yu | A61B 17/221 606/159 |
| 2016/0058458 A1 * | 3/2016 | Hansen | A61B 17/221 606/200 |
| 2016/0157985 A1 * | 6/2016 | Vo | A61B 17/221 606/200 |
| 2016/0158038 A1 * | 6/2016 | Teitelbaum | A61F 2/90 623/1.11 |
| 2016/0220269 A1 * | 8/2016 | Labropoulos | A61B 17/320725 |
| 2016/0256180 A1 * | 9/2016 | Vale | A61B 17/22 |
| 2016/0338820 A1 * | 11/2016 | Tejani | A61F 2/01 |
| 2016/0346507 A1 * | 12/2016 | Jackson | A61M 25/0053 |
| 2016/0346508 A1 * | 12/2016 | Williams | A61M 25/0053 |
| 2017/0056061 A1 * | 3/2017 | Ogle | A61B 17/320725 |
| 2017/0119409 A1 * | 5/2017 | Ma | A61B 17/221 |
| 2017/0182290 A1 * | 6/2017 | Stern | A61M 25/0053 |
| 2017/0215900 A1 | 8/2017 | Lowinger et al. | |
| 2017/0238950 A1 * | 8/2017 | Yang | A61M 25/0009 |
| 2017/0312069 A1 | 11/2017 | Sachar et al. | |
| 2018/0235743 A1 * | 8/2018 | Farago | A61F 2/013 |
| 2018/0250150 A1 * | 9/2018 | Majercak | A61B 17/3468 |
| 2018/0296235 A1 | 10/2018 | Ulm, III | |
| 2018/0296315 A1 | 10/2018 | Nguyen et al. | |

FOREIGN PATENT DOCUMENTS

| | | |
|---|---|---|
| WO | 0107101 A1 | 2/2001 |
| WO | 2016113047 A1 | 7/2016 |

OTHER PUBLICATIONS

Maegerlein et al., "Intraprocedural ThrombusFragmentation During Interventional Stroke Treatment: A Comparison of Direct Thrombus Aspiration and Stent Retriever Thrombectomy," Abstract Only, accessed from http://Ups:l/dialog—proqueslcanl'professional/dllC\4fN11905129760/15D5689541 E64CA296<Y3?accounlid=157282, ProQuest, Jul. 2017, 4 pp.

International Preliminary Report on Patentability from International Application No. PCT/US2019/018993, dated Sep. 10, 2020, 9 pp.

\* cited by examiner

CATHETER INCLUDING AN EXPANDABLE MEMBER

TECHNICAL FIELD

This disclosure relates to a medical catheter.

BACKGROUND

A medical catheter defining at least one lumen has been proposed for use with various medical procedures. For example, in some cases, a medical catheter may be used to access and treat defects in blood vessels, such as, but not limited to, lesions or occlusions in blood vessels.

SUMMARY

In some aspects, this disclosure describes example catheters including an elongated body comprising an inner liner, an outer jacket, a structural support member positioned between at least a portion of the inner liner and at least a portion of the outer jacket, and an expandable member distal to the structural support member at a distal portion of the elongated body. The expandable member is configured to expand radially outward within a vessel of a patient, e.g., to engage a clot. This disclosure also describes examples of methods of forming the catheters described herein and methods of using the catheters.

Clause 1: In one example, a catheter comprises an elongated body including a proximal portion and a distal portion, the elongated body comprising: an inner liner; an outer jacket; a structural support member positioned between at least a portion of the inner liner and at least a portion of the outer jacket; and an expandable member mechanically coupled to the structural support member at the distal portion of the elongated body, wherein the expandable member is configured to expand radially outward.

Clause 2: In some examples of the catheter of clause 1, the expandable member is at least one of welded, soldered, bonded, or hooked to the structural support member.

Clause 3: In some examples of the catheter of clause 1 or 2, the expandable member is mechanically coupled to the structural support member at a plurality of circumferential positions of the structural support member.

Clause 4: In some examples of the catheter of clause 3, the expandable member comprises a plurality of struts defining a plurality of cells, wherein proximal peaks of at least one strut of the plurality of struts are coupled to the structural support member.

Clause 5: In some examples of the catheter of any of clauses 1-4, the expandable member is configured to self-expand.

Clause 6: In some examples of the catheter of clause 5, the catheter further comprises a retractable sheath positioned over the expandable member, the retractable sheath configured to be retracted proximally to allow the expandable member to self-expand from a collapsed configuration to an expanded configuration.

Clause 7: In some examples of the catheter of any of clauses 1-6, the expandable member is configured to engage a clot.

Clause 8: In some examples of the catheter of clause 7, an inner surface of the expandable member comprises a surface treatment configured to promote at least one of mechanical or chemical engagement between the inner surface and the clot.

Clause 9: In some examples of the catheter of clause 8, the surface treatment comprises at least one of surface etching, a positive electrical charge, and a cationic polymer such as polylysine.

Clause 10: In some examples of the catheter of any of clauses 1-9, a proximal end of the expandable member is at least one of positioned over at least a portion of the inner liner, or positioned under at least a portion of the outer jacket.

Clause 11: In some examples of the catheter of clause 10, the inner liner comprises a first section and a second section distal to the first section, the structural support member positioned over the first section and the expandable member positioned over the second section, and wherein the second section of the inner liner has a lower modulus of elasticity than the first section.

Clause 12: In some examples of the catheter of clause 10 or 11, the inner liner comprises a first section and a second section distal to the first section, the structural support member positioned over the first section and the expandable member positioned over the second section, and wherein the second section of the inner liner has a lower coefficient of friction than the first section.

Clause 13: In some examples of the catheter of any of clauses 10-12, the inner liner comprises a first section and a second section distal to the first section, the structural support member positioned over the first section and the expandable member positioned over the second section, and wherein the second section of the inner liner is configured to have a higher affinity to a clot than the first section of the inner liner.

Clause 14: In some examples of the catheter of any of clauses 10-13, the inner liner comprises a first section and a second section distal to the first section, the structural support member positioned over the first section and the expandable member positioned over the second section, and wherein an inner surface of the second section is configured to promote at least one of mechanical or chemical clot engagement.

Clause 15: In some examples of the catheter of clause 14, the inner surface of the second section of the inner liner is etched to promote mechanical clot engagement.

Clause 16: In some examples of the catheter of any of clauses 1-15, the expandable member is configured to expand radially outward from a collapsed configuration to an expanded configuration, wherein the expandable member defines a funnel shape when in the expanded configuration.

Clause 17: In some examples of the catheter of clause 16, in the expanded configuration, a cross-section of the expandable member is wider at a distal end than at a proximal end.

Clause 18: In some examples of the catheter of clause 17, in the expanded configuration, the cross-section of the expandable member at the distal end is from about 150 percent to about 300 percent wider than an inner diameter of the proximal portion of the elongated body.

Clause 19: In some examples of the catheter of any of clauses 1-18, the elongated body comprises an electrical conductor electrically coupled to the expandable member, the expandable member configured to receive an electrical signal via the electrical conductor that causes the expandable member to electrostatically engage a clot.

Clause 20: In some examples of the catheter of clause 19, the expandable member is configured to expand radially outward in response to receiving the electrical signal.

Clause 21: In some examples of the catheter of any of clauses 1-20, the outer jacket comprises a first section and a second section distal to the first section, the first section positioned over the structural support member and the second section positioned over the expandable member, wherein the second section of the outer jacket comprises a thermoplastic, elastomeric polymer configured to accommodate radial expansion of the expandable member.

Clause 22: In some examples of the catheter of any of clauses 1-21, the outer jacket extends over at least a portion of the expandable member.

Clause 23: In some examples of the catheter of clause 22, the outer jacket and the inner liner mechanically couple the expandable member to the structural support member.

Clause 24: In some examples of the catheter of any of clauses 1-23, the structural support member and the expandable member are integrally formed.

Clause 25: In some examples of the catheter of any of clauses 1-24, the structural support member and the expandable member are within a same radial layer of the elongated body.

Clause 26: In some examples of the catheter of any of clauses 1-25, at least a portion of the expandable member forms an interior surface of a lumen defined by the elongated body.

Clause 27: In an example, a catheter comprises: an elongated body comprising: an inner liner; an outer jacket; a structural support member; and an expandable member distal to the structural support member, wherein the structural support member and at least a portion of the expandable member are positioned between the inner liner and the outer jacket.

Clause 28: In some examples of the catheter of clause 27, the structural support member abuts the expandable member.

Clause 29: In some examples of the catheter of clause 27 or 28, a proximal end of the expandable member is spaced from a distal end of the structural support member.

Clause 30: In some examples of the catheter of any of clauses 27-29, the expandable member is at least one of welded, soldered, bonded, or hooked to the structural support member.

Clause 31: In some examples of the catheter of any of clauses 27-31, the expandable member is mechanically coupled to the structural support member at a plurality of circumferential positions of the structural support member.

Clause 32: In some examples of the catheter of clause 31, the expandable member comprises a plurality of struts defining a plurality of cells, wherein proximal peaks of the plurality of struts are coupled to the structural support member.

Clause 33: In some examples of the catheter of any of clauses 27-32, the expandable member is configured to self-expand.

Clause 34: In some examples of the catheter of clause 33, the catheter further comprises a retractable sheath positioned over the expandable member, the retractable sheath configured to be retracted proximally to allow the expandable member to self-expand from a collapsed configuration to an expanded configuration.

Clause 35: In some examples of the catheter of any of clauses 27-34, the expandable member is configured to engage a clot.

Clause 36: In some examples of the catheter of clause 35, an inner surface of the expandable member comprises a surface treatment configured to promote at least one of mechanical or chemical engagement between the inner surface and the clot.

Clause 37: In some examples of the catheter of clause 36, the surface treatment comprises at least one of surface etching, a positive electrical charge, and a cationic polymer such as polylysine.

Clause 38: In some examples of the catheter of any of clauses 27-37, a proximal end of the expandable member is at least one of positioned over at least a portion of the inner liner, or positioned under at least a portion of the outer jacket.

Clause 39: In some examples of the catheter of clause 38, the inner liner comprises a first section and a second section distal to the first section, the structural support member positioned over the first section and the expandable member positioned over the second section, and wherein the second section of the inner liner has a lower modulus of elasticity than the first section.

Clause 40: In some examples of the catheter of clause 38 or 39, the inner liner comprises a first section and a second section distal to the first section, the structural support member positioned over the first section and the expandable member positioned over the second section, and wherein the second section of the inner liner has a lower coefficient of friction than the first section.

Clause 41: In some examples of the catheter of any of clauses 38-40, the inner liner comprises a first section and a second section distal to the first section, the structural support member positioned over the first section and the expandable member positioned over the second section, and wherein the second section of the inner liner is configured to have a higher affinity to a clot than the first section of the inner liner.

Clause 42: In some examples of the catheter of any of clauses 38-41, the inner liner comprises a first section and a second section distal to the first section, the structural support member positioned over the first section and the expandable member positioned over the second section, and wherein an inner surface of the second section is configured to promote at least one of mechanical or chemical clot engagement.

Clause 43: In some examples of the catheter of clause 42, the inner surface of the second section of the inner liner is etched to promote mechanical clot engagement.

Clause 44: In some examples of the catheter of any of clauses 27-43, the expandable member configured to expand radially outward from a collapsed configuration to an expanded configuration, wherein the expandable member defines a funnel shape when in the expanded configuration.

Clause 45: In some examples of the catheter of clause 44, the expanded configuration, a cross-section of the expandable member is wider at a distal end than at a proximal end.

Clause 46: In some examples of the catheter of clause 45, the expanded configuration, the cross-section of the expandable member at the distal end is from about 150 percent to about 300 percent wider than an inner diameter of a proximal portion of the elongated body.

Clause 47: In some examples of the catheter of any of clauses 27-46, the elongated body comprises an electrical conductor electrically coupled to the expandable member, the expandable member configured to receive an electrical signal via the electrical conductor that causes the expandable member to electrostatically engage a clot.

Clause 48: In some examples of the catheter of clause 47, the expandable member is configured to expand radially outward in response to receiving the electrical signal.

Clause 49: In some examples of the catheter of any of clauses 27-48, the outer jacket comprises a first section and a second section distal to the first section, the first section positioned over the structural support member and the second section positioned over the expandable member, wherein the second section of the outer jacket comprises a thermoplastic, elastomeric polymer configured to accommodate radial expansion of the expandable member.

Clause 50: In some examples of the catheter of any of clauses 27-49, the outer jacket extends over at least a portion of the expandable member.

Clause 51: In some examples of the catheter of clause 50, the outer jacket and the inner liner mechanically couple the expandable member to the structural support member.

Clause 52: In some examples of the catheter of any of clauses 27-51, the structural support member and the expandable member are integrally formed.

Clause 53: In some examples of the catheter of any of clauses 27-52, at least a portion of the expandable member forms an interior surface of a lumen defined by the elongated body.

Clause 54: In an example, a method comprises: introducing a catheter into vasculature of a patient, the catheter comprising an elongated body including a proximal portion and a distal portion, the elongated body comprising: an inner liner; an outer jacket; a structural support member positioned between at least a portion of the inner liner and at least a portion of the outer jacket; and an expandable member mechanically coupled to the structural support member at the distal portion of the elongated body, wherein the expandable member is configured to expand radially outward; and expanding the expandable member from a collapsed configuration to an expanded configuration within the vasculature of the patient.

Clause 55: In some examples of the method of clause 54, expanding the expandable member comprises retracting a sheath covering the expandable member to expose the expandable member.

Clause 56: In some examples of the method of clause 54 or 55, expanding the expandable member comprises applying electrical energy to the expandable member.

Clause 57: In some examples of the method of any of clauses 54-56, the method further comprises, after expanding the expandable member, applying suction to the catheter to aspirate material through the expandable member and into an inner lumen of the catheter.

Clause 58: In some examples of the method of any of clauses 54-57, the method further comprises removing the catheter from the vasculature.

Clause 59: In some examples of the method of clause 57, the method further comprises inhibiting distal movement of the material relative to the catheter via the expandable member.

Clause 60: In some examples of the method of clause 59, inhibiting distal movement of the material via the expandable member comprises entangling the material in the expandable member.

Clause 61: In some examples of the method of clause 59 or 60, inhibiting distal movement of the material via the expandable member comprises frictionally engaging the material with an inner wall of the expandable member.

Clause 62: In some examples of the method of any of clauses 54-61, the expandable member comprises an expandable tube or funnel.

The examples described herein may be combined in any permutation or combination.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

The disclosure describes a medical device, referred to herein as a catheter, that includes a relatively flexible elongated body configured to be navigated through vasculature of a patient, e.g., tortuous vasculature in a brain of the patient. The elongated body may include an inner liner, an outer jacket, and a structural support member (e.g., a coil or a braid) positioned between at least a portion of the inner liner and outer jacket. A distal portion of the elongated body includes an expandable member, such as an expandable stent-like structure or an expandable funnel, positioned distal to a proximal end of the structural support member. The expandable member may be configured to expand radially outward within a vessel of the patient. This may enable, for example, the expandable member to engage with a clot (e.g., thrombus or embolism) during an aspiration procedure, such as, but not limited to, a medical procedure using A Direct Aspiration first Pass Technique (ADAPT) for acute stroke thrombectomy. The expandable member may help improve aspiration of the clot into the catheter by providing a relatively large diameter and interior space for the clot to engage with the elongated body compared to examples in which an otherwise similar catheter does not include an expandable member. For example, such a catheter that does not include an expandable member may have limited radial expansion due to a structural support member that extends to the distal end of the catheter, and may thus make it harder to aspirate a clot (e.g., due to a smaller cross-sectional dimension of the distal end of the catheter). The expandable member may overcome such radial expansion limitations, including by increasing clot engagement, reducing the amount of time required for revascularization, and increase revascularization success rates for various procedures, as compared to similar procedures used with catheters that do not include an expandable member to engage a clot.

Figure 1:
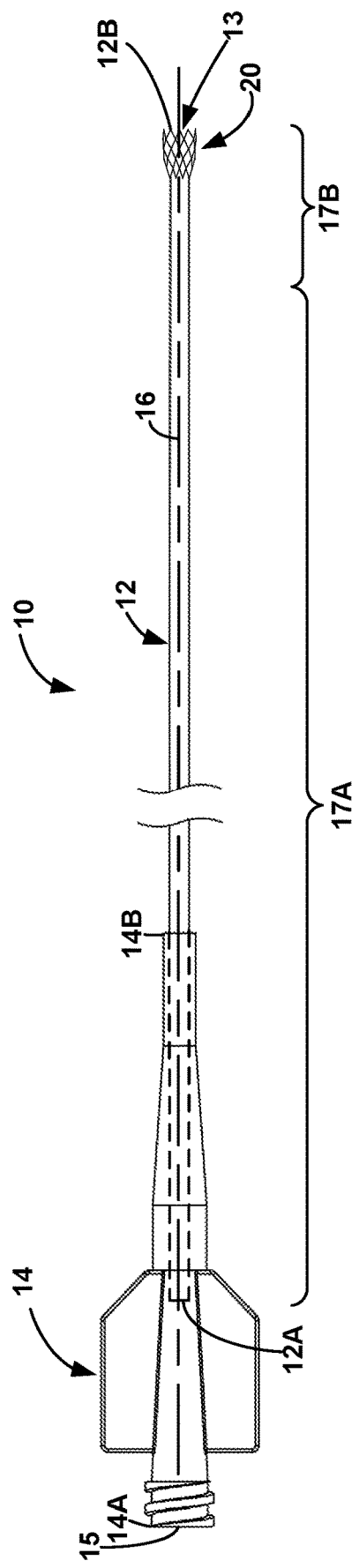
FIG. 1 is a conceptual side view of an example catheter, which includes an elongated body and an expandable member at a distal portion of the elongated body.
Figure 2:
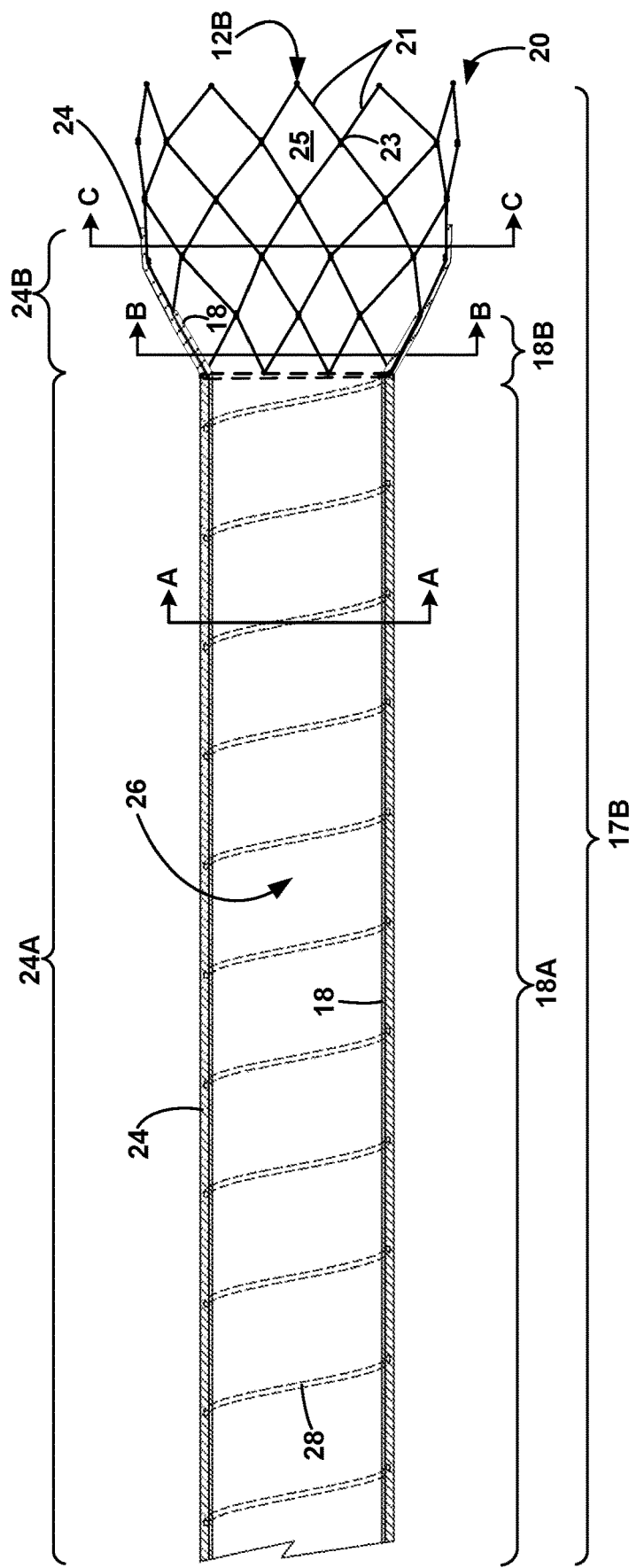
FIGS. 2 to 7 are conceptual cross-sectional views of examples of the distal portion of the elongated body of FIG. 1, where the cross-section is taken through a center of the elongated body and along a longitudinal axis.

FIGS. 1 and 2 are conceptual side views of an example catheter 10, which includes an elongated body 12 and a hub 14. Elongated body 12 includes a proximal portion 17A and a distal portion 17B. FIG. 2 shows an enlarged conceptual cross-sectional view of distal portion 17B of elongated body 12, where the cross-section is taken through a center of elongated body 12 along a longitudinal axis 16 of elongated body 12.

Elongated body 12 is configured to be advanced through vasculature of a patient via a pushing force applied to proximal portion 17A (e.g., via hub 14) of elongated body 12 without buckling, kinking, or otherwise undesirably deforming (e.g., ovalization). Elongated body 12 includes an inner liner 18, an outer jacket 24, and a structural support member 28 positioned between at least a portion of inner liner 18 and at least a portion of outer jacket 24. At distal portion 17B, elongated body 12 includes an expandable member 20 adjacent to structural support member 28 and configured to radially expand within a vessel of a patient, e.g., to engage a clot within the vessel.

Elongated body 12 extends from proximal end 12A to distal end 12B and defines at least one inner lumen 26 (shown in FIG. 2). In the example shown in FIG. 1, proximal end 12A of elongated body 12 is received within hub 14 and is mechanically connected to hub 14 via an adhesive, welding, or another suitable technique or combination of techniques. Inner lumen 26 may be defined by portions of hub 14 and inner liner 18. Catheter 10 may be used as an aspiration catheter to remove a clot or other material such as plaques or foreign bodies from vasculature of a patient. In such examples, a vacuum may be applied to proximal end 14A of catheter 10 (e.g., via hub 14) to draw a clot or other blockage into inner lumen 26. An aspiration catheter may be used in various medical procedures, such as a medical procedure to treat an ischemic insult, which may occur due to occlusion of a blood vessel (arterial or venous) that deprives brain tissue, heart tissue or other tissues of oxygen-carrying blood.

In some examples, catheter 10 is configured to access relatively distal locations in a patient including, for example, the middle cerebral artery (MCA), internal carotid artery (ICA), the Circle of Willis, and tissue sites more distal than the MCA, ICA, and the Circle of Willis. The MCA, as well as other vasculature in the brain or other relatively distal tissue sites (e.g., relative to the vascular access point), may be relatively difficult to reach with a catheter, due at least in part to the tortuous pathway (e.g., comprising relatively sharp twists or turns) through the vasculature to reach these tissue sites. Elongated body 12 may be structurally configured to be relatively flexible, pushable, and relatively kink- and buckle-resistant, so that it may resist buckling when a pushing force is applied to a relatively proximal section of catheter 10 (e.g., via hub 14) to advance elongated body 12 distally through vasculature, and so that it may resist kinking when traversing around a tight turn in the vasculature. In some examples, elongated body 12 is configured to substantially conform to the curvature of the vasculature. In addition, in some examples, elongated body 12 has a column strength and flexibility that allow at least distal portion 17B of elongated body 12 to be navigated from a femoral artery, through the aorta of the patient, and into the intracranial vascular system of the patient, e.g., to reach a relatively distal treatment site.

Although primarily described as being used to reach relatively distal vasculature sites, catheter 10 may also be configured to be used with other target tissue sites. For example, catheter 10 may be used to access tissue sites throughout the coronary and peripheral vasculature, the gastrointestinal tract, the urethra, ureters, fallopian tubes, veins and other body lumens.

In some examples, catheter 10 may be described in terms of the working length of elongated body 12. The working length of elongated body 12 may be measured from distal end 14B of hub 14 (e.g., a distal end of a strain relief member of a hub assembly) to distal end 12B of elongated body 12 along longitudinal axis 16. The working length of catheter 10 may depend on the location of the target tissue site within the body of a patient or may depend on the medical procedure for which catheter 10 is used. For example, if catheter 10 is a distal access catheter used to access vasculature in a brain of a patient from a femoral artery access point at the groin of the patient, elongated body 12 may have a working length of about 115 centimeters (cm) to about 145 cm or more, such as about 130 cm, although other lengths may be used. Distal portion 17B may be about 5 cm to about 35 cm in length. The length of distal portion 17B may include the length of expandable member 20. Proximal portion 17A may be about 90 cm to about 130 cm in length, depending on the length of distal portion 17B.

Hub 14 may be positioned at a proximal portion 17A of elongated body 12. Hub 14 may define the proximal end 14A of catheter 10 and may include an opening 15 aligned with inner lumen 26 of elongated body 12, such that inner lumen 26 of elongated body 12 may be accessed via opening 15 and, in some examples, closed via opening 15. For example, hub 14 may include a luer connector, a hemostasis valve, or another mechanism or combination of mechanisms for connecting hub 14 to another device such as a vacuum source for performing the aspiration techniques described herein. In some examples, proximal end 14A of catheter 10 can include another structure in addition to, or instead of, hub 14.

In some cases, a clinician may steer catheter 10 through the vasculature of a patient by pushing or rotating hub 14 and/or proximal portion 17A of catheter 10 to navigate distal portion 17B of elongated body 12 through the vasculature of a patient. The clinician may apply torque to hub 14 and/or proximal portion 17A of the catheter 10 (or at least a portion of elongated body 12 that is more proximal than distal portion 17B implanted in the patient) in order to rotate distal portion 17B of catheter 10.

In some examples, inner liner 18 of elongated body 12 defines at least a portion of inner lumen 26 of elongated body 12, inner lumen 26 defining a passageway through elongated body 12. As discussed in further detail below, expandable member 20 may also define at least a portion of inner lumen 26. In some examples, inner lumen 26 may extend over the entire length of inner liner 18 (e.g., from proximal end 12A to the distal end of inner liner 18). Inner lumen 26 may be sized to receive a medical device (e.g., another catheter, a guidewire, an embolic protection device, a stent, or any combination thereof), a therapeutic agent, or the like. Inner liner 18 may define a single inner lumen 26, or multiple inner lumens (e.g., two inner lumens or three inner lumens) of catheter 10.

Inner lumen 26 formed by inner liner 18 may define the inner diameter of elongated body 12. The diameter of inner lumen 26 (as measured in a direction perpendicular to a longitudinal axis 16 of elongated body 12) may vary based on the one or more procedures with which catheter 10 may be used. In some examples, the diameter of inner lumen 26 of elongated body 12, also referred to herein as an inner diameter of elongated body 12 or inner liner 18, may be substantially constant (e.g., constant or nearly constant) from proximal end 12A to the proximal end of expandable member 20 (e.g., substantially constant apart from the diameter change associated with expandable member 20). In some examples, the inner diameter may be about 1.524 mm (about 0.060 inches) or larger. In other examples, the inner diameter may not be constant. For example, the inner diameter of elongated body 12 may taper from a first inner diameter at proximal end 12A to a second, smaller inner diameter at a more distal section just proximal to expandable member 20. For example, an inner diameter of elongated body 12 may taper from a first inner diameter of about 0.0685 inches (about 1.74 mm) to a second inner diameter of about to 0.0605 inches (about 1.54 mm). The inner diameter may, for example, gradually taper in the direction along longitudinal axis 16, where the taper can be linear, curved, continuous, or discontinuous; e.g., the inner diameter of inner liner 18 may step-down from the first inner diameter to the second inner diameter in discrete steps. As described further below, the inner diameter of the section of elongated body 12 that includes expandable member 20 may be larger than the inner diameter of elongated body 12 within regions proximal to expandable member 20.

Inner liner 18 may be formed using any suitable material, such as, but not limited to, polytetrafluoroethylene (PTFE), expanded PTFE (ePTFE, e.g., unidirectional ePTFE or bi-directional ePTFE), a fluoropolymer, perfluoroalkyoxy alkane (PFA), fluorinated ethylene propylene (FEP), polyolefin elastomers or any combination thereof. A unidirectional ePTFE may be stretched in one of the longitudinal or radial directions, and a bi-directional ePTFE may be stretched in both the longitudinal and radial directions. Other examples of materials from which inner liner 18 may be formed include, but are not limited to, Low Density Polyethylene (LDPE) (e.g., about 42 D), a PTFE having a durometer of about 60 D, High Density Polyethylene (HDPE), or any combination thereof. Some such polyolefin materials may have similar coefficients of friction as PTFE, and may be conducive to processing. In some examples, inner liner 18 may include PTFE, which may provide elongated body 12 with a lubricious inner surface and allow relatively easy delivery of interventional devices through the elongated body, removal of a clot, or relatively easy tracking of the elongated body over a guide member (e.g., a guidewire or a microcatheter). In some cases, a PTFE inner liner 18 may impart stiffness to elongated body 12 to improve various navigation properties such as the pushability catheter 10 through vasculature of the patient.

Inner liner 18 can be formed from one or more tubular sections of the same material or different materials that are joined together using any suitable technique, such as an adhesive, fusing/welding, co-extrusion, or any combination thereof. For example, different materials may be selected for different sections of inner liner 18 in order to achieve different structural properties and performance attributes of elongated body 12. In some examples, the different various tubular sections may include similar polymeric constructions whose relative properties have been selected to result in sections of different relative hardnesses or other properties for improved navigability of elongated body 12 or improved engagement of elongated body 12 with a clot.

In some examples, one or more portions of the inner surface of inner liner 18 defining inner lumen 26 may be lubricious to facilitate the introduction and passage of a medical device (e.g., another catheter, a guide member, an embolic protection device, a stent, a thrombectomy device, or any combination thereof), a therapeutic agent, a clot, or the like, through lumen 26. Examples of therapeutic agents include, but are not limited to, an oxygenated medium or a pharmaceutical agent, which may be, for example, a vasodilator such as nifedipine or sodium nitroprusside, or a tissue plasminogen activator (t-PA), which can be used to breakdown blood clots. In some examples, the material from which portions of inner liner 18 is formed may itself be lubricious (e.g., PTFE). In addition to, or instead of, being formed from a lubricious material, in some examples, an inner surface of inner liner 18 is coated with a lubricious coating such as a hydrophilic coating.

In some examples, one or more sections of inner liner 18 at distal portion 17B may be configured to have a relatively high affinity to the clot material by, for example, using a suitable surface treatment (e.g., a coating and/or etching) on inner liner 18 to promote mechanical or chemical engagement with the clot. (Such affinity may be measured, for example, with a DMA (dynamic mechanical analyzer) equipped with a shear sandwich clamp.) For example, the inner surface of a distal section 18B of inner liner 18 may be treated with a surface coating, etching, or other roughening mechanism, so that distal section 18B better engages with the clot, such that the inner surface of distal section 18B may be configured to promote at least one of mechanical or chemical clot engagement. A roughened or less lubricious surface of inner liner 18 that is brought in contact with the clot may allow for the clot to stick better to inner liner 18, which may allow the clot to be pulled into catheter 10 more effectively. Examples of suitable coating materials to increase the affinity of the clot to inner liner 18 may include, for example, a thermoplastic elastomer such as Chrono-Prene™ (AdvanSource Biomaterials, Wilmington, Mass.), ChronoPrene™ (AdvanSource Biomaterials, Wilmington, Mass.), ChronoPrene™ 5A, ChronoPrene™ 15A; a polyolefin elastomer such as ethylene-octene or ethylene-butene copolymer, for example, ENGAGE™ Polyolefin Elastomers (Dow Chemical Company, Midland, Mich.), ENGAGE™ 8107, 7367, 7270; or the like.

In some examples, distal section 18B of inner liner 18 may be configured to have a higher affinity to the clot than proximal section 18A of inner liner 18.

In the example shown in FIG. 2, inner liner 18 includes a proximal section 18A (e.g., a first section of inner liner 18) and a distal section 18B (e.g., a second section of inner liner 18). In some examples, proximal section 18A is coaxial with and coextensive with structural support member 28. In other examples, however, proximal section 18A may not be coaxial with and/or not coextensive with structural support member 28. As an example, a distal end of proximal section 18A may terminate proximal to a distal end of structural support member 28, such that structural support member 28 extends distally past the distal end of proximal section 18A. As another example, a distal end of proximal section 18A may terminate distal to a distal end of structural support member 28, such that proximal section 18A of inner liner 18 extends distally past the distal end of structural support member 28.

Figure 3:
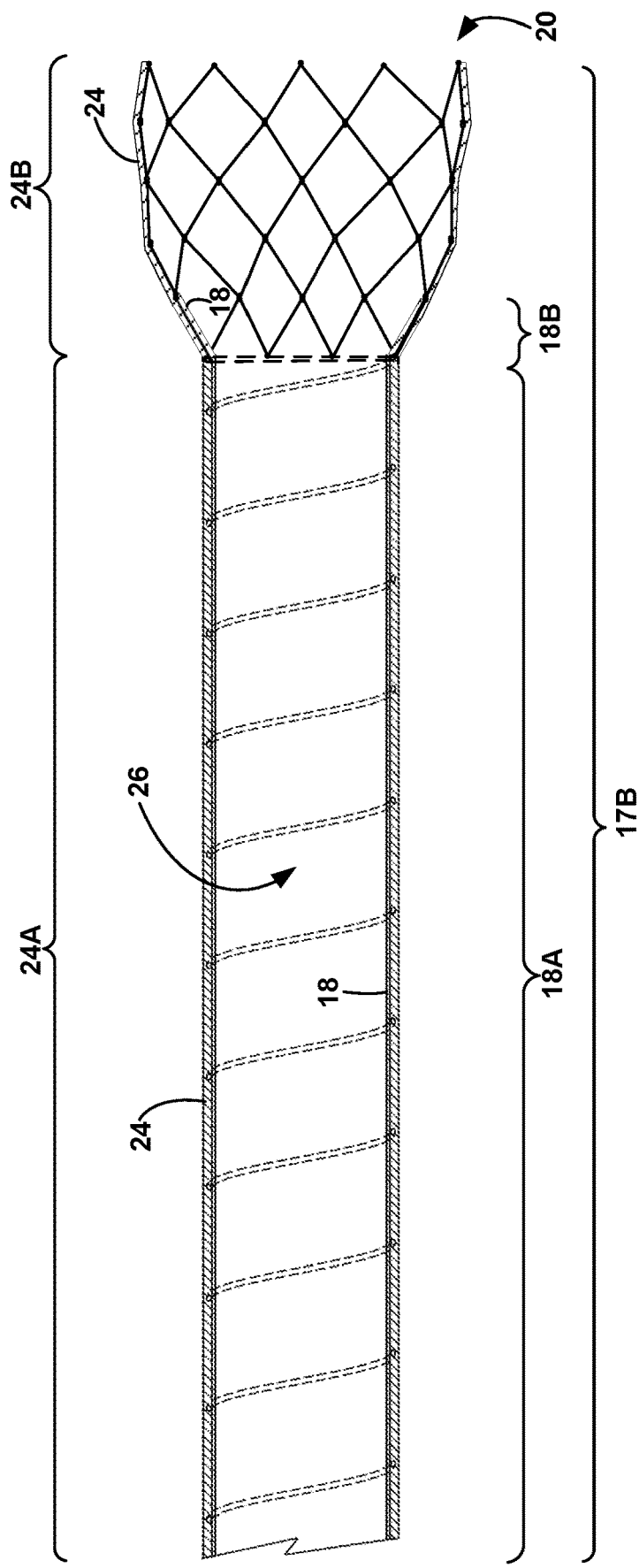
Figure 4:
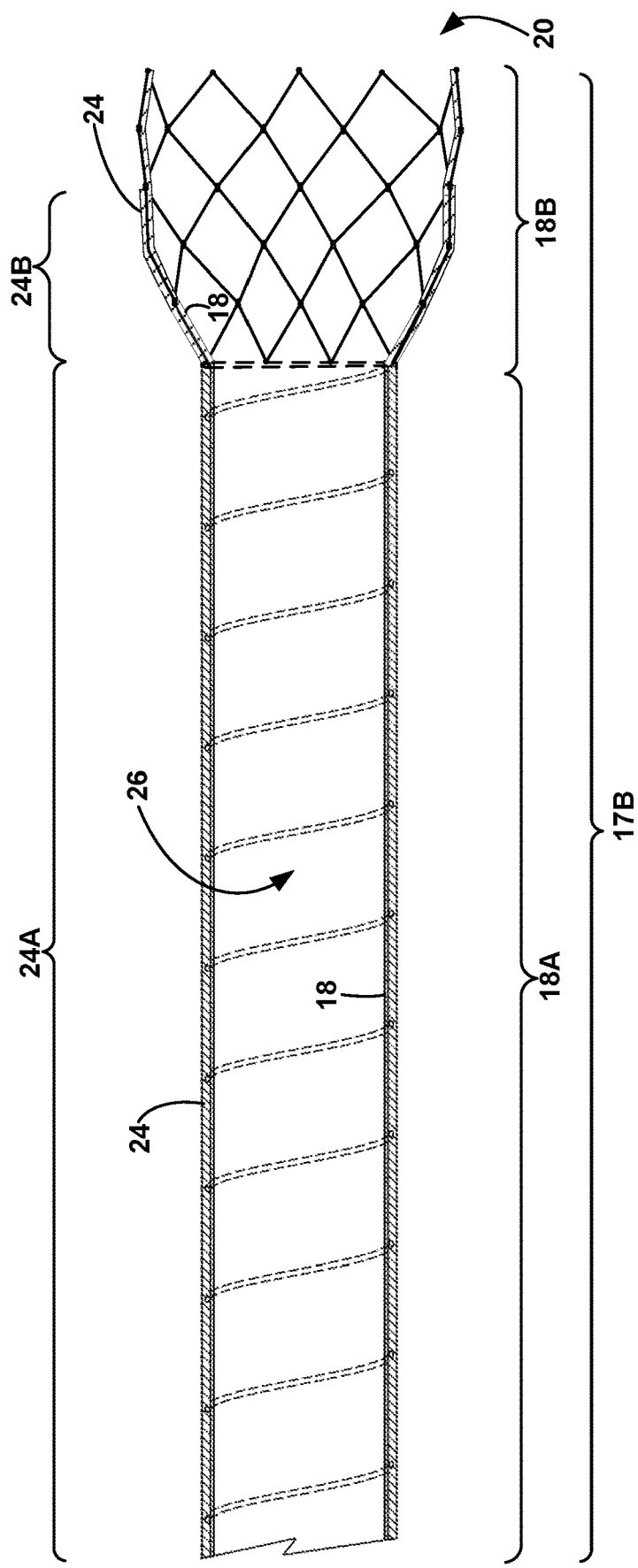
Figure 5:
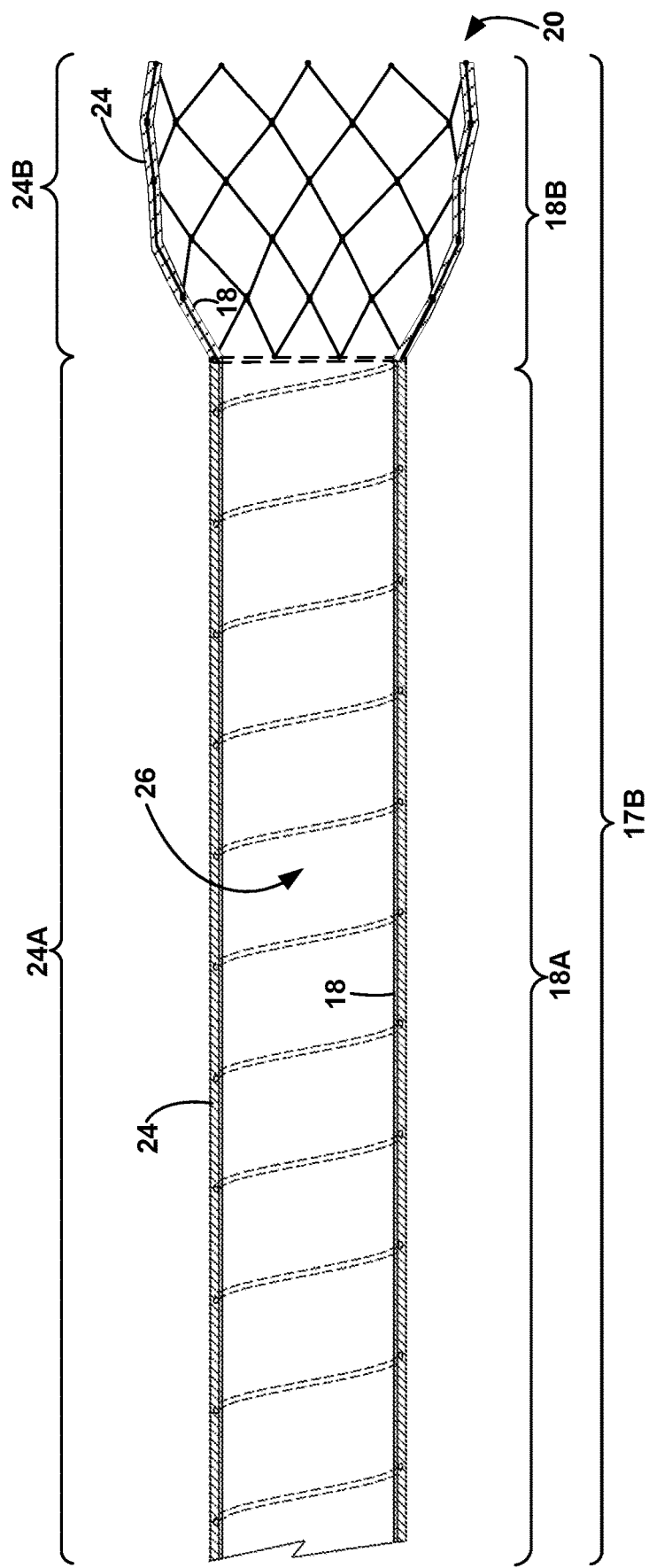

Distal section 18B of inner liner 18 may be co-axial with expandable member 20. In some examples, as shown in FIG. 2, distal section 18B of inner liner 18 may terminate prior to the distal end of expandable member 20, such that expandable member 20 extends distally past a distal end of inner liner 18 (e.g., as shown in FIGS. 2 and 3). In other examples, however, distal section 18B of inner liner 18 may be coextensive with expandable member 20 (e.g., as shown in FIGS. 4 and 5).

In some examples, proximal section 18A and distal section 18B of inner liner 18 may together extend the entire length of inner liner 18 measured along longitudinal axis 16. For example, proximal section 18A may extend from proximal end 12A of elongated body 12 to the point where distal section 18B begins (e.g., where structural support member 28 meets with expandable member 20) and distal section 18B may extend within all or a portion of expandable member 20. In other examples, inner liner 18 may include additional sections along elongated body 12 to alter the properties of catheter 10 over various portions of the working length.

Proximal section 18A and distal section 18B may comprise different materials and/or surface treatments. In some of these examples, proximal section 18A and distal section 18B of inner liner 18 may be formed as separate structures that are attached together to define a butt joint or another suitable union. In other examples, proximal section 18A and distal section 18B of inner liner 18 may have a unitary body construction (e.g., may be formed as one body, such that inner liner 18 is a single, seamless tubular body). A seamless inner liner 18 may, for example, be devoid of any seams (e.g., the seam formed from joining two separate tubular bodies together at an axial location along longitudinal axis 16), such that the seamless inner liner 18 is a unitary body, rather than multiple, discrete bodies that are separately formed and subsequently connected together. A seamless inner liner 18 may be easier to slide over another device, e.g., a guide member, compared to a catheter formed from two or more longitudinal sections that are mechanically connected to each other because the seamless inner liner may define a smoother inner lumen 26. In contrast, joints between sections of an inner liner that are formed from two or more longitudinal sections may define surface protrusions or other irregularities along inner lumen 26 which may interfere with the passage of devices through inner lumen 26. In addition, a seamless inner liner 18 may help distribute pushing and rotational forces along the length of elongated body 12. In some such examples, distal section 18B and proximal section 18A of inner liner 18 may formed of the same material or different materials that that formed into a unitary body construction (e.g., through a coextrusion process).

In some examples, proximal section 18A and distal section 18B are formed from different materials that possess different structural characteristics. For example, distal section 18B of inner liner 18 may include a softer material that can more readily radially expand to accommodate the expansion of expandable member 20 compared to material from which proximal section 18A is formed. As another example, distal section 18B of inner liner 18 may have a lower coefficient of friction than proximal section 18A of inner liner 18, a lower modulus of elasticity than proximal section 18A, a lower stiffness (e.g., more flexible material) than proximal section 18A, or any combination thereof. The stiffness of inner liner 18 can be measured by, for example, a flexural stiffness or a torsional stiffness value. Inner liner 18 that includes proximal section 18A having a greater stiffness than distal section 18B may enable elongated body 12 to exhibit a more flexible tip while still retaining sufficient strength and rigidity throughout the majority of elongated body 12 for navigation. Additionally, or alternatively, the materials for distal section 18B may be selected to provide better engagement (e.g., mechanical or chemical engagement) with the clot.

In some examples, distal section 18B may include a surface treatment that provides better engagement with a clot (e.g., mechanical or chemical engagement). Proximal section 18A of inner liner 18 may include the same or similar surface treatment, or may not include the same or similar surface treatment as distal section 18B. In some medical procedures, distal section 18B engages with a clot before proximal section 18A when the clot is being aspirated through a distal end of elongated body 12, and, therefore, it may be desirable for distal section 18B to be configured for better clot engagement than proximal section 18A so as to prevent/inhibit undesired movement of clot distally out of distal section 18B or catheter 10. Proximal section 18A may be configured for better passage of medical devices through inner lumen 26, e.g., may define a more lubricious passageway than distal section 18B.

Elongated body 12 includes one or more structural support members 28 positioned over inner liner 18. Structural support member 28 is configured to increase the structural integrity of elongated body 12 while allowing elongated body 12 to remain relatively flexible. For example, structural support member 28 may be configured to help elongated body 12 substantially maintain its cross-sectional shape (e.g., circular or nearly circular) or at least help prevent elongated body 12 from buckling or kinking as it is navigated through tortuous anatomy. Additionally, or alternatively, structural support member 28, together with inner liner 18, and outer jacket 24, may help distribute both pushing and rotational forces along a length of elongated body 12, which may help prevent kinking of elongated body 12 upon rotation of body 12 or help prevent buckling of body 12 upon application of a pushing force to body 12. As a result, a clinician may apply pushing forces, rotational forces, or both, to the proximal portion of elongated body 12, and such forces may cause a distal portion of elongated body 12 to advance distally, rotate, or both, respectively.

Structural support member 28 may include one or more tubular braided structures, one or more coil members defining a plurality of turns, e.g., in the shape of a helix, or a combination of a braided structure and a coil member. Thus, although the examples of the disclosure primarily describe structural support member 28 as a coil, in other examples, catheter 10 may include a braided structure instead of a coil, a braided structure in addition to a coil, or a combination that includes one or more of each structure. As one example, a proximal portion of structural support member 28 may include a braided structure and a distal portion of structural support member 28 may include a coil member. In some examples, a braided wire (e.g., a combination of round wires and flat wires) may provide elongated body 12 with better ovalization resistance and tensile strength compared to other catheter designs (e.g., a support element consisting of only one metal coil or a braid consisting of only round wires) and coil structures (e.g., wire coils) may exhibit better columnar strength (e.g., kink resistance) and/or hoop strength (e.g., resistance to ovalization) compared to other catheter designs.

Structural support member 28 can be made from any suitable material, such as, but not limited to, a metal (e.g., a nickel titanium alloy (Nitinol), stainless steel, tungsten, titanium, gold, platinum, palladium, tantalum, silver, or a nickel-chromium alloy, a cobalt-chromium alloy, or the like), a polymer, a fiber, or any combination thereof. In some examples, structural support member 28 may include one or more metal wires braided or coiled around inner liner 18. The metal wires may include round wires, flat-round wires, flat wires, or any combination thereof. Round wires may be substantially circular in cross-section and flat wires may be a quadrilateral in cross-section, where the cross-sections are taken in a direction orthogonal to the longitudinal axis of the respective wire when the wire is substantially straight. The cross-sectional dimension of the wire (e.g., the diameter) can sometimes be referred to as the size of the wire. For example, a 0.0015 inch (0.0381 mm) round wire may have a circular cross-sectional diameter of about 0.0015 inches and a 0.001×0.008 inch (0.0254×0.2032 mm) flat wire may have cross-sectional dimensions of about 0.001 inches and about 0.008 inches. In some examples, structural support member 28 may include metal wires defining area between about 0.001 inches and about 0.008 inches.

In other examples, structural support member 28 may include a spiral cut hypotube that is expanded and positioned over inner liner 18. As described further below, in some such examples, structural support member 28 may be formed integrally with expandable member 20. For example, structural support member 28 and expandable member 20 may be laser cut from the same hypotube, e.g., structural support member 28 representing a spiral cut segment of the hypotube and expandable member 20 representing a lattice/strut cut segment of the hypotube.

As shown in FIG. 2, structural support member 28 may extend along only a portion of a length of elongated body 12 and is positioned proximal to expandable member 20. In some examples, the distal end of structural support member 28 may abut the proximal end of expandable member 20 and may be coupled to expandable member 20 (e.g., mechanically coupled or bonded with adhesive, or welded). In other examples, expandable member 20 may not be coupled to structural support member 28 or may not be in direct contact (e.g., abutting contact) with structural support member 28, although the two members may be in the same radial layer of elongated body 12. For example, the distal end of structural support member 28 may be adjacent to the proximal end of expandable member 20 but separated by a small gap. In such examples, structural support member 28 and expandable member 20 may be in the same radial layer and inner liner 18, outer jacket 24, or both may secure both expandable member 20 and structural support member 28 in place along elongated body 12.

In some examples, structural support member 28 may be coupled, adhered, or mechanically connected to at least a portion of an outer surface of inner liner 18. For example, structural support member 28 may be positioned over inner liner 18 and secured in place (e.g., fixed) relative to inner liner 18 by outer jacket 24 using a melt-reflow/heat shrink process, or other suitable technique.

Additionally, or alternatively, structural support member 28 may be secured to inner liner 18 with the assistance of a support layer (not shown) that helps adhere structural support member 28 to one or both inner liner 18 or outer jacket 24. The support layer may include a thermoplastic material or a thermoset material, such as a thermoset polymer or a thermoset adhesive that bonds to inner liner 18, outer jacket 24, or both. In some cases, the material forming the support layer may have elastic properties, such that there may be a tendency for the support layer to return to a resting position. In some examples, the support layer is positioned over the entire length of structural support member 28 and inner liner 18. In other examples, the support layer is only positioned over a part of the length of structural support member 28 and inner liner 18.

Elongated body 12 also includes outer jacket 24 positioned over structural support member 28 and inner liner 18, the structural support member 28 being positioned between portions of inner liner 18 and outer jacket 24. In some examples, outer jacket 24 may be positioned around structural support member 28 such that outer jacket 24 covers at least a part or all of both inner liner 18 and structural support member 28. Outer jacket 24, together with inner liner 18 and structural support member 28, may be configured to define elongated body 12 having the desired structural characteristics (e.g., flexibility, kink resistance, torque responsiveness, structural integrity, pushability, and column strength, which may be a measure of a maximum compressive load that can be applied to elongated body 12 without taking a permanent set). For example, outer jacket 24 may have stiffness characteristics that contribute to the desired stiffness profile of elongated body 12.

In some examples, outer jacket 24 may be formed to have a stiffness that decreases from a proximal end 12A of elongated body 12 toward distal end 12B. The lowered stiffness of outer jacket 24 within the distal portion 17B of elongated body 12 may improve the flexibility and navigability of catheter 10 through tortious vasculature of the patient, while the relatively higher stiffness of outer jacket 24 within the proximal portion 17A of catheter 10 may provide better pushability or kink resistance. In some examples, outer jacket 24 may be formed from two or more different materials with different mechanical properties that enable outer jacket 24 to exhibit the desired stiffness characteristics. In some examples, the stiffness of outer jacket 24 may be characterized in terms of the relative durometer (shore hardness) of the jacket material. In some examples, the hardness of outer jacket 24 may be between a Shore A hardness of about 30 and a Shore D hardness of about 85. For example, outer jacket 24 may have a hardness of less than about 30 A within distal portion 17B to provide flexibility and expandability, while outer jacket 24 may have a Shore D hardness between about 55 and about 85 within proximal portion 17A to provide improved stiffness and navigability.

Additionally, or alternatively, outer jacket 24 may have a stiffness of less than about 15 A-30 A within a distal section 24B of outer jacket 24 that is at least partially coextensive with expandable member 20. In some examples outer jacket 24 may define a stiffness within a proximal section 24A (e.g., a first section of outer jacket 24) that is greater than the stiffness with distal section 24B (e.g., a second section of outer jacket 24). Distal section 24B of outer jacket 24 may be configured to accommodate radial expansion of expandable member 20.

Additionally, or alternatively, outer jacket 24 may define a durometer gradient (e.g., hardness) along longitudinal axis 16. For example, outer jacket 24 may be defined by a plurality of tubular segments extending from proximal end 12A toward distal end 12B wherein each tubular segment defines a different durometer. The durometer gradient of outer jacket 24 may be selected to help provide elongated body 12 with the desired flexibility characteristics. For example, in some examples in which elongated body 12 increases in flexibility from proximal end 12A towards distal end 12B, the durometer gradient of outer jacket 24 may decrease in a direction from proximal end 12A towards distal end 12B. In some examples, the durometer of outer jacket 24 may be from about 25 D to about 75 D. For example, outer jacket 24 may define a durometer gradient from proximal end 12A towards distal end 12B that generally decreases from about 75 D to about 25 D.

In some examples, outer jacket 24 may be formed using any suitable material including, but are not limited to, polymers, such as a polyether block amide (e.g., PEBAX®, commercially available from Arkema Group of Colombes, France), an aliphatic polyamide (e.g., Grilamid®, commercially available from EMS-Chemie of Sumter, S.C.), another thermoplastic elastomer (e.g., a thermoplastic, elastomeric polymer configured to accommodate radial expansion of expandable member 20), polyurethanes, polyamides, or other thermoplastic material, or combinations thereof. In some examples, outer jacket 24 may be formed of an elastic material, such as polyolefin thermoplastic elastomers, polyurethane elastomeric alloys or silicone, that permits the expansion of expandable member 20. For example, distal section 24B of outer jacket 24 extending at least partially coextensive with expandable member 20 may be formed with such elastic material.

Outer jacket 24 may be heat shrunk around structural support member 28 and, in some examples, at least a portion (e.g., a proximal portion) of expandable member 20 to secure the two members in the same radial layer. In some examples, during the heat shrinking of outer jacket 24 around structural support member 28, the material of outer jacket 24 may flow into at least some of the inner spacings or gaps (e.g., gaps between the adjacent turns of the coils, or between the struts or braids) within structural support member 28 or expandable member 20 such that portions of outer jacket 24 and structural support member 28 or expandable member 20 form a pseudo coextensive layer.

In some examples, at least a portion of an outer surface of outer jacket 24 includes one or more coatings, such as, but not limited to, an anti-thrombogenic coating, which may help reduce the formation of thrombi in vitro, an antimicrobial coating, and/or a lubricating coating. In some examples, the lubricating coating may be configured to reduce static friction or kinetic friction between elongated body 12 and tissue of the patient as elongated body 12 is advanced through the vasculature. In addition, or instead, in some examples, the lubricating coating may be configured to reduce static or kinetic friction between elongated body 12 and another catheter through which elongated body 12 may be inserted. The lubricating coating can be, for example, a hydrophilic coating. In some examples, the entire working length of elongated body 12 (from distal end 14B of hub 14 to the distal end of outer jacket 24) may be coated with the hydrophilic coating. In other examples, only a portion of the working length of elongated body 12 coated with the hydrophilic coating. This may provide a length of elongated body 12 distal from distal end 14B of hub 14 with which the clinician may grip elongated body 12, e.g., to rotate elongated body 12, pull elongated body 12 when removing elongated body 12 from the patient, or push elongated body 12 through vasculature.

Although a coating or another material may be applied over the outer surface of outer jacket 24, outer jacket 24 may still substantially define shape and size of the outer surface of elongated body 12. In some examples, the outer diameter of elongated body 12 may be substantially constant (e.g., constant or nearly constant) along the length of elongated body 12, excluding the change in diameter created by expandable member 20. In other examples, the outer diameter of elongated body 12 may taper from the first outer diameter within proximal portion 17A of elongated body 12 to a second outer diameter at point proximate to the proximal end of expandable member 20 (e.g., at point where expandable member 20 is coupled to or positioned next to structural support member 28), and the outer diameter may increase from the referenced point to a third outer diameter of the section of elongated body 12 where expandable member 20 is positioned.

In some examples, the taper of the outer diameter of elongated body 12 (e.g., from the first diameter to the second diameter or from the second diameter to the third diameter) may be continuous along the length of elongated body 12, such that an outer surface of elongated body 12 defines a smooth transition between different diameter portions. In other examples, elongated body 12 may define discrete step-downs in outer diameter to define the taper. The size of the discrete step-downs in diameter may be selected to reduce the number of edges that may catch on anatomical features within the vasculature as elongated body 12 is advanced through vasculature.

A larger diameter proximal portion of elongated body 12 may provide better proximal support for elongated body 12, which may help increase the pushability of elongated body 12. In addition, a generally smaller diameter within the distal portion (e.g., excluding the diameter of expandable member 20) may increase the navigability of elongated body 12 through tortuous vasculature. Thus, by reducing the outer diameter of elongated body 12 from proximal portion 17A to distal portion 17B, elongated body 12 may better traverse through tortuous vasculature while still maintaining a relatively high level of proximal pushability. In some examples, such as when expandable member 20 is in a collapsed configuration, the outer diameter at distal end 12B may be the same or smaller than the second outer diameter proximal to distal end 12B. In some examples, the outer diameter(s) of elongated body 12 is in a range of about 3 French to about 10 French, such as about 3 French to about 6 French. The measurement term French, abbreviated Fr or F, is three times the diameter of a device as measured in mm. For example, a 6 French diameter is about 2 mm.

Elongated body 12 also includes expandable member 20 positioned at distal portion 17B of elongated body 12, such that a distal end of expandable member 20 defines distal end 12B of elongated body 12. Expandable member 20 may be a stent-like structure or an expandable funnel configured to provide a radially expandable distal end 12B with a relatively large diameter (compared to, for example, proximal portion 17A of elongated body 12) and interior space for better engagement with a clot (e.g., thrombus or embolus). In some examples, catheter 10 may be used with an aspiration procedure (e.g., ADAPT technique) and the size and shape of expandable member 20 may enable elongated body 12 to better engage a clot by increasing the opening into which the clot may be received, and/or by distributing the aspiration forces over a greater portion of the clot rather than a localized area, thereby allowing the clot to be aspirated into catheter 10.

By incorporating expandable member 20 into the design of catheter 10, catheter 10 may offer several advantages over conventional aspiration catheters. For example, by constructing catheter 10 with only structural support member 28 (e.g., at the exclusion of expandable member 20), catheter 10 may exhibit one or more desired navigability characteristics (e.g., strength, flexibility, kink-resistance, or the like), but would exhibit limited to no expandability at the distal end. To improve the aspiration efficiency, the diameter of the catheter may be increased to provide engagement with the clot, but the increased diameter may reduce the overall navigability of the catheter through vasculature of the patient. The inclusion of expandable member 20 may allow catheter 10 may allow the diameter of elongated body 12 (e.g., within proximal portion 17A) to remain relatively small and exhibit the improved navigability characteristics of catheter body with a small diameter, while expandable member 20 would provide catheter 10 with the improved engagement and suction characteristics that may be attributed to having a large diameter distal end 12B In some examples, the presence of expandable member 20 may lead to improved revascularization success rates, such as due to the improved clot engagement (e.g., to better pull the entirety of the clot into catheter 10 during aspiration) as described herein.

In an expanded configuration, expandable member 20 may define a funnel shape. For example, expandable member 20 may taper from a relatively small cross-sectional dimension near the proximal end of expandable member 20 to a relatively large cross-sectional dimension at distal end 12B. In some examples, the cross-section may be round (e.g., circularly shaped) and the cross-sectional axis may be referred to as a diameter. In some examples, the cross-section may be irregularly shaped, in which case the cross-sectional dimension may be referred to as the major axis (e.g., a longest dimension of the cross-section). In an example, in the expanded configuration, the cross-section of expandable member 20 may be wider at a distal end than a proximal end. For example, in the expanded configuration, the distal end of expandable member 20 may be about 150 percent to about 300 percent wider than an inner diameter of proximal portion 17A of elongated body 12.

In an example, the increased diameter at distal end 12B may allow for better sealing capabilities with the vessel wall and better engagement with a clot during aspiration. For example, during aspiration with a conventional catheter, engagement with the clot may be reduced due to the relatively small diameter of the catheter at its distal tip. Additionally, due to the size of the catheter relative to the vessel diameter, spacing between the interior of the vessel wall and the exterior of the catheter can result in a general loss of suction power. In contrast, the increased diameter of expandable member 20 may provide better sealing with the vessel wall thereby resulting in a reduced loss of suction. Additionally, in examples where the cross-section is generally round, the increased diameter and funnel shape of expandable member 20 may allow for a large portion of the clot to be received within the inner volume defined by the funnel shape to provide improved sealing and physical engagement with the clot during the aspiration procedure.

In some examples, expandable member 20 may resemble a stent-like structure that includes a tubular body comprising a plurality of struts 21 (e.g., an individual straight portion of an undulating ring) that are interconnected via one or more connections at adjacent vertices 23 (peaks or valleys) to define a plurality of cells 25 between adjacent struts 21, such as diamond shape cells or other cell designs. In the example of FIG. 2, the two labeled struts 21 form a vertex 23 that together point in a proximal direction. In general, each of the struts 21 of expandable member 20 may be a substantially straight portion (e.g., a straight or nearly straight member) that may join with one or more other struts 21 at a respective vertex 23. In some examples, struts 21 may each remain substantially straight before and after expansion of the expandable member 20. However, struts 21 may move relative to each other (e.g., pivoting at vertices 23 relative to adjacent struts 21) when expandable member 20 expands from the collapsed configuration to the expanded configuration. In some examples, one or more proximal peaks of at least one strut of the plurality of struts (e.g., struts 21) may be coupled to structural support member 28.

Struts 21 may be forced apart and radially outward from one another (e.g., via straitening of the undulating rings) to increase the diameter at various portions of expandable member 20. In other examples, expandable member 20 may include an expandable mesh (e.g., woven sleeve or woven tubular structure) or other design.

Expandable member 20 can be made from any suitable material, such as, but not limited to, a metal (e.g., a nickel titanium alloy (Nitinol), stainless steel, tungsten, titanium, gold, platinum, palladium, tantalum, silver, or a nickel-chromium alloy, a cobalt-chromium alloy, or the like), a polymer, a fiber, or any combination thereof. In some examples, expandable member 20 may be formed from a shape memory metal (e.g., nickel titanium (Nitinol)). The materials of expandable member 20 may be selected so that once in an expanded configuration, expandable member 20 substantially maintains its shape, even in the presence of the vacuum force applied to catheter 10 during the aspiration process.

Expandable member 20 may be of any suitable length and diameter, which may be selected based on the target vessel or particular procedure being performed. In some examples, expandable member 20 may be about 2 centimeters to about 25 centimeters long measured in a direction parallel to longitudinal axis 16 and configured to expand to about 150 percent to about 300 percent of the outer diameter of its collapsed configuration. As discussed above, in some examples, in the collapsed state, expandable member 20 may have a cross-sectional dimension equal to or substantially equal to the outer diameter of elongated body 12 proximate to expandable member 20. In an example, expandable member 20 may be about 1.5 cm, about 2.0 cm, or about 25 cm in length. In some examples, in the expanded configuration, distal end 12B of expandable member 20 may be about 150 percent to about 300 percent of the diameter of the proximal end of expandable member 20. In some examples, the expanded outer diameter or the cross-sectional dimension of elongated body 12 at distal end 12B may be about 200 percent, 250 percent, 300 percent, or another percentage larger compared to a portion of elongated body 12 that includes only structural support member 28 (e.g., the diameter or cross-section at line A-A of FIG. 2). In some examples, to the expandability of expandable member 20 at distal portion 17B may allow the cross-sectional dimension of elongated body 12 within proximal portion 17A to remain comparatively small. As described above, such a combination may allow catheter 10 to exhibit the improved navigability characteristics of catheter body with a small diameter while still providing catheter 10 with the improved engagement and suction characteristics that may be attributed to having a large diameter distal end 12B.

In some examples, expandable member 20 may be mechanically coupled to structural support member 28 and/or layered between (at least in a proximal portion of the expandable member 20) inner liner 18 and outer jacket 24. For example, expandable member 20 and structural support member 28 can be formed independently of one another, and the proximal end of expandable member 20 may be coupled to the distal end of structural support member 28. In some examples, expandable member 20 and structural support member 28 may be joined via welding, brazing, soldering, epoxy, or other suitable technique. In some examples, expandable member 20 may be welded, soldered, bonded, or hooked to structural support member 28. In the example shown in FIG. 2, expandable member 20 comprises a plurality of struts that define a plurality of cells. One or more of the proximal peaks of the proximal most strut (e.g., at the proximal end of expandable member 20) may be coupled to structural support member 28 such that expandable member 20 is mechanically coupled to structural support member 28 at a plurality of circumferential positions around structural support member 28, such as shown in FIGS. 2 through 6. In some examples, expandable member 20 may be bonded (e.g., glued), hooked (e.g., mechanically interlocked), or coupled to structural support member 28 using other means.

In some examples, structural support member 28 and expandable member 20 may be integrally formed. For example, structural support member 28 may include a plurality of wires (e.g., coils or braids) that are subsequently woven to form expandable member 20, such that the manufacture may not necessarily require welding or other assembly or connection of expandable member 20 to structural support member 28. In other examples, structural support member 28 and expandable member 20 may be formed using the same hypotube; the proximal portion of the hypotube being spirally cut to form a coil structure (e.g. structural support member 28) while the distal portion of the hypotube is cut to form a plurality of interconnected struts that form expandable member 20.

Additionally, or alternatively, expandable member 20 may be at least partially secured to structural support member 28 via inner liner 18 and/or outer jacket 24. For example, expandable member 20 may not be directly coupled to structural support member 28 or may not be in direct contact (e.g., abutting contact) with structural support member 28, although the two members may be in the same radial layer of elongated body 12. In an example, expandable member 20 may be positioned adjacent to structural support member 28 over inner liner 18, and outer jacket 24 may be positioned over expandable member 20 and structural support member 28. Outer jacket 24 may be heat shrunk over the two members such that outer jacket 24 secures both expandable member 20 and structural support member 28 in place relative to inner liner 18. In such examples, expandable member 20 may be positioned at least partially between inner liner 18 and outer jacket 24 (e.g., layered or positioned between distal section 18B of inner liner 18 and distal section 24B of outer jacket 24). For example, at least a proximal portion of expandable member 20 may be positioned between inner liner 18 and outer jacket 24 (e.g., as shown in FIGS. 2-5 and 7). One or both of inner liner 18 or outer jacket 24 may extend over the entire length of expandable member 20 or may extend over only a portion of the length of expandable member 20. For example, distal section 18B of inner liner 18 may extend over only part of the length of expandable member 20 leaving portions of expandable member 20 exposed to inner lumen 26 (e.g., FIG. 3). The exposed portions of expandable member 20 may provide better engagement with a clot and/or prevent distal migration of clot from catheter 10 due to the texture of expandable member 20 or direct electrostatic engagement with expandable member 20. For example, as described herein, elongated body 12 may comprise an electrical conductor electrically coupled to expandable member 20, and expandable member 20 may be configured to receive an electrical signal via the conductor that causes expandable member 20 to electrostatically engage the clot. In some examples, expandable member 20 may be configured to expand radially outward in response to receiving the electrical signal.

In some examples, an inner surface of expandable member 20 may comprise a surface treatment configured to promote at least one of mechanical or chemical engagement between the inner surface and the clot. In some examples, a coating may be applied to portions of the inner surface of expandable member 20 (e.g., the inner surface of the struts) or the inner surface of inner liner 18, or the surfaces may be textured via etching or otherwise roughened (or rougher) in comparison to the outer surface of the expandable member 20 to better mechanically engage the clot. In some examples, the inner surface of the distal section 18B of inner liner 18 may be etched, such as to promote mechanical clot engagement.

In some examples, clot engagement with expandable member 20 may be enhanced by delivering electrical energy to expandable member 20. For example, a source of electrical energy (e.g., an electrical signal generator) may deliver an electrical signal to expandable member 20 via one or more electrical conductors (not shown) electrically coupled to expandable member 20. The electrical energy may be positively charged to electrostatically engage a clot. Characteristics of the electrical energy may be adjusted to better engage the clot, such as polarity, or an amount or type of current delivered. For example, pulsed direct current may be employed, optionally with a non-square and/or non-negative waveform. The electrical conductors can extend through inner lumen 26 of elongated body 12, can extend along an outer surface of elongated body 12, can be embedded in a wall of elongated body 12, or have any other suitable configuration.

Expandable member 20 may expand from a collapsed configuration to an expanded configuration using any suitable technique. In some examples, expandable member 20 may be balloon expandable. For example, once elongated body 12 is positioned within the vessel of a patient adjacent a target treatment site, a balloon (not shown) may be introduced through lumen 26 and inflated to radially expand expandable member 20 from a collapsed configuration to an expanded configuration. Once in the expanded configuration, expandable member 20 may maintain its shape to allow the balloon to be deflated and removed. Expandable member 20 may then be collapsed for removal from the vessel of the patient by, for example, pulling elongated body 12 or at least expandable member 20 into an outer sheath having an inner lumen with a diameter less than the diameter of an expanded expandable member 20. The outer sheath may apply an inward force to expandable member 20 as expandable member 20 is retracted into the outer sheath.

In other examples, expandable member 20 may be configured to self-expand. For example, expandable member 20 may be formed from a shape memory material such as Nitinol. In some such examples as described further below, catheter 10 may include a retractable sheath over expandable member 20 that helps retain expandable member 20 in a collapsed configuration, e.g., during navigation of elongated body 12 to a target treatment site within the vasculature of a patient. Once at the target treatment site, the retractable sheath may be withdrawn proximally over elongated body 12 to allow expandable member 20 to self-expand. In other examples, an electrical energy may be used to expand expandable member 20. For example, expandable member 20 (or a portion or a layer thereof) may be formed from a material or metal that bends or deflects in response to a current passed therethrough (or to heat generated as a result of such current). One such type of material is shape memory alloy actuator material, e.g. nitinol or Flexinol™ available from Dynalloy, Inc. of Irvine, Calif. USA.

Although FIG. 2 illustrates an example in which both inner liner 18 and outer jacket 24 terminate proximal to a distal end of expandable member 20, in other examples, inner liner 18 and outer jacket 24 can have other arrangements relative to expandable member 20. FIGS. 3 to 7 illustrate other example arrangements of inner liner 18, expandable member 20, and outer jacket 24. FIGS. 3 to 7 are conceptual cross-sectional views of additional examples of distal portion 17B of elongated body 12 of FIG. 1, where the cross-section is taken through a center of the elongated body and along longitudinal axis 16. In each of the examples shown in FIGS. 3 to 7, a distal section 18B of inner liner 18 may be coaxial with expandable member 20, and outer jacket 24 may be coaxial with expandable member 20. In general, in some examples, a proximal end of expandable member 20 may be at least one of positioned over at least a portion of inner liner 18, or positioned under at least a portion of outer jacket 24, such as described with respect to FIGS. 3 through 7 below.

In the example of FIG. 3, distal section 18B of inner liner 18 extends only partially coextensively with expandable member 20 in a longitudinal direction, such that inner liner 18 terminates proximal to a distal end of expandable member 20. Distal section 24B of outer jacket 24 may be completely coextensive (also referred to herein as coterminous) with expandable member 20, such that a distal end of distal section 24B terminates at the same point as the distal end of expandable member 20. In an example, because distal section 18B of inner liner 18 extends only partially coextensively with expandable member 20, an inner surface of expandable member 20 may be exposed (e.g., partially define) lumen 26. In some examples, at least a portion of expandable member 20 may form an interior surface of lumen 26 defined by elongated body 12. The exposed inner surface of expandable member 20 may enhance clot engagement and/or prevent distal migration of clot during aspiration or withdrawal (e.g., due to surface treatment of the inner surface or due to electrical energy that may be applied to expandable member 20 to engage the clot, or due to the "grip" properties of the exposed portions of the mesh of struts and cells).

In other examples, as shown in FIG. 4, distal section 18B of inner liner 18 can be coaxial and completely coextensive with expandable member 20. In the example shown in FIG. 4, distal section 24B of outer jacket 24 is coaxial with expandable member 20, but extends only partially coextensively with expandable member 20 in a longitudinal direction. In particular, distal section 24B of outer jacket 24 terminates proximal to a distal end of expandable member 20. In an example, because distal section 24B of outer jacket 24 extends only partially coextensively with expandable member 20, a portion of the outer surface of expandable member 20 may be exposed (e.g., not covered by outer jacket 24), which may allow expandable member 20 to expand more easily. In an example, because distal section 18B of inner liner 18 may be coaxial and completely coextensive with expandable member 20, distal section 18B of inner liner 18 may better engage the clot (e.g., due material characteristics of inner liner 18 or due to a surface treatment of inner liner 18).

In the example of FIG. 5, both distal section 18B of inner liner 18 and distal section 24B of outer jacket 24 are coaxial and completely coextensive with expandable member 20. In an example, because expandable member 20 may be at least substantially covered (e.g., fully covered or nearly covered) by inner liner 18 and outer jacket 24, expandable member 20 may not necessarily need to be exposed to the clot or other bodily materials of the patient. For example, the expandable member 20 may be selected based on structural characteristics without necessarily requiring selection based on clot engagement characters (e.g., electrical conduction or strut pattern).

Figure 6:
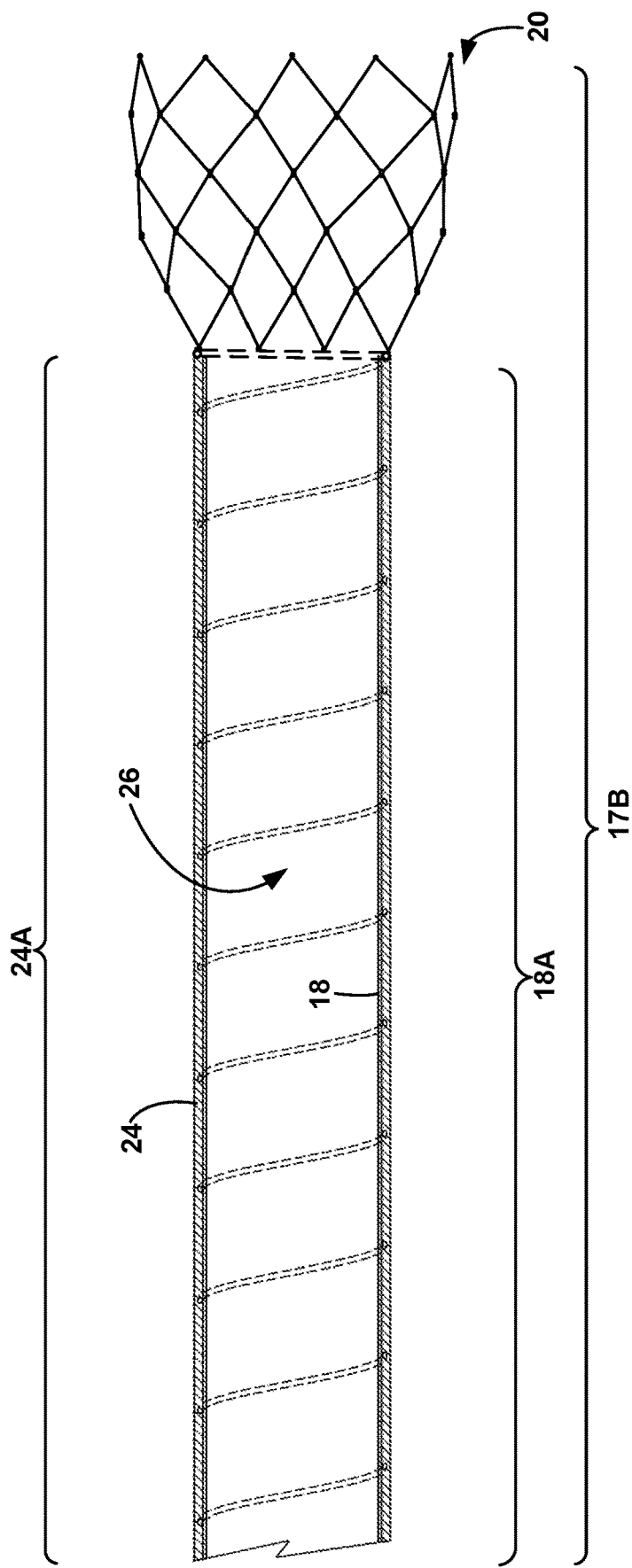

In the example of FIG. 6, inner liner 18 is defined only by proximal section 18A (e.g., inner liner 18 does not include a section that extends coextensively with expandable member 20. Similarly, outer jacket 24 is defined only by proximal section 24A (e.g., outer jacket 24 does not include a section that extends coextensively with expandable member 20). In an example, because expandable member 20 may not necessarily be covered by inner liner 18 or outer jacket 24, flexibility and expandability of expandable member 20 may be increased (e.g., allow expandable member 20 to expand radially outward more easily).

Figure 7:
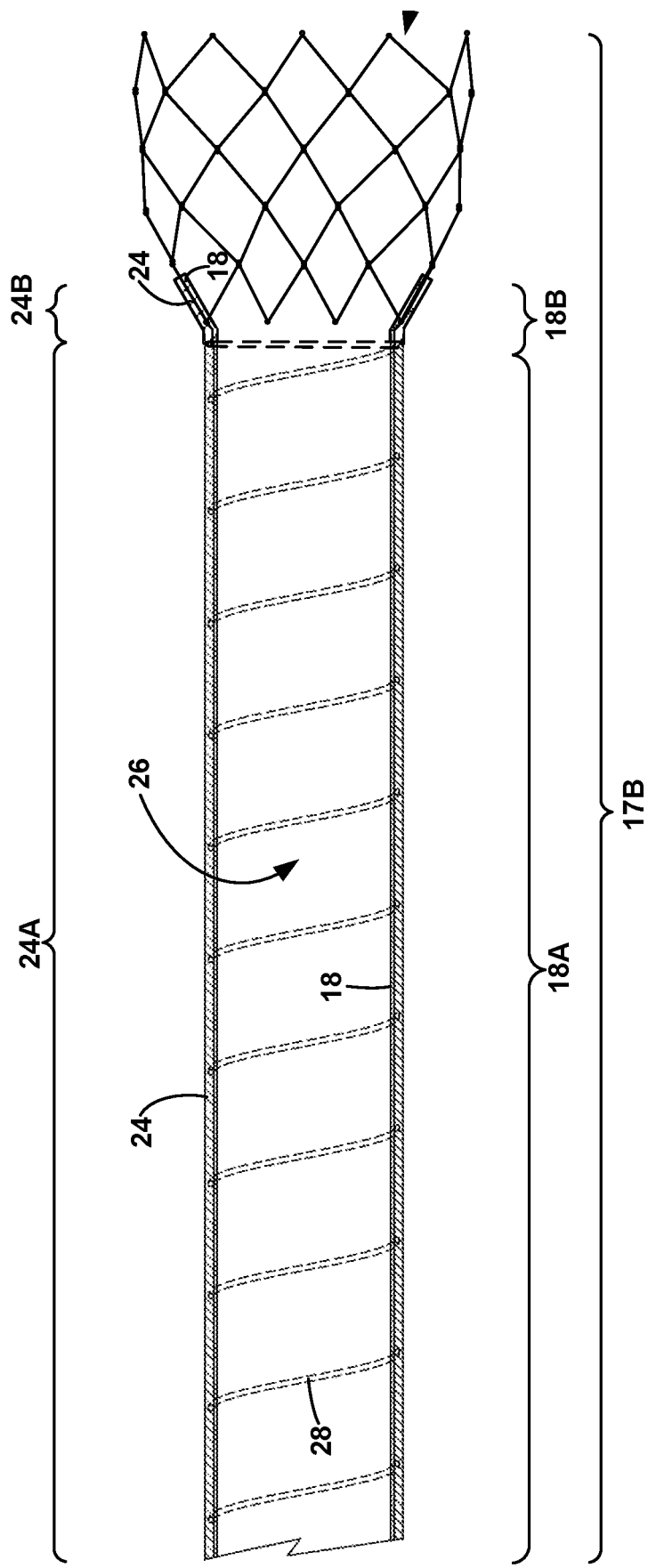

In the example, of FIG. 7, expandable member 20 is partially secured between inner liner 18 and outer jacket 24 and adjacent to support member 28, but expandable member 20 may not necessarily be directly coupled to structural support member 28. Although shown in the expanded configuration, expandable member 20 may be in the same radial layer as structural support member 28 (e.g., positioned or layered between inner liner 18 and outer jacket 24), even if not directly coupled to structural support member 28. In the example of FIG. 7, distal section 18B of inner liner 18 and distal section 24B of outer jacket 24 each extend only partially coextensively with expandable member 20 in a longitudinal direction. In an example, because expandable member 20 may not necessarily be required to be directly coupled to structural support member 28, distal portion 17B may be more flexible.

Elements of the example catheters described herein may be combined in any suitable arrangement. For example, in some examples expandable member 20 may be secured between only inner liner 18 and outer jacket 24 (e.g., not directly coupled to structural support member 28, where a proximal end of expandable member 20 may be spaced from a distal end of structural support member 28) as shown in FIG. 7 and distal section 18B and/or distal section 24B may be completely coextensive with expandable member 20 as shown in FIG. 3,4, or 5.

Figure 8:
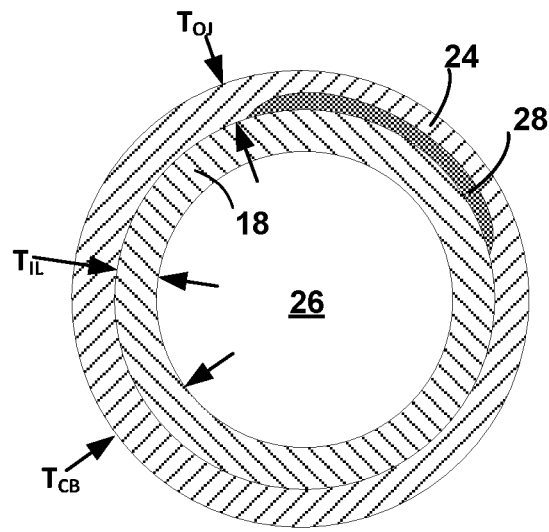
FIG. 8 is a conceptual cross-sectional view of the elongated body of FIG. 2 taken along line A-A in FIG. 2.
Figure 9:
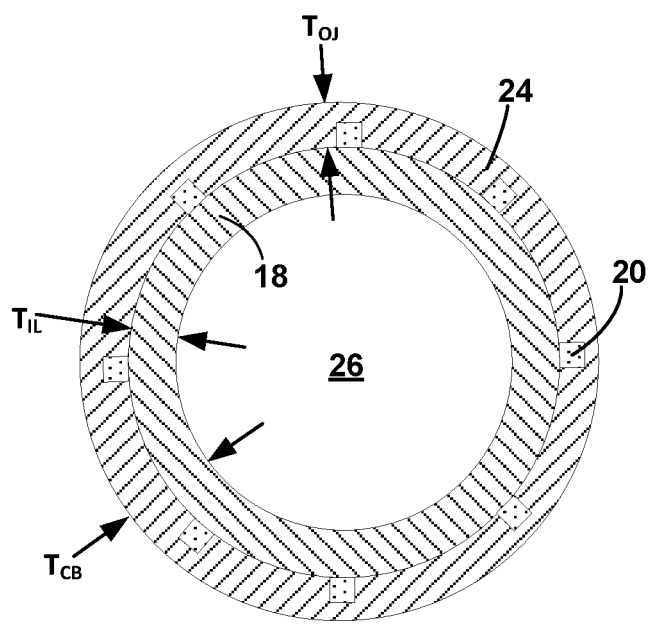
FIG. 9 is a conceptual cross-sectional view of the elongated body of FIG. 2 taken along line B-B in FIG. 2.
Figure 10:
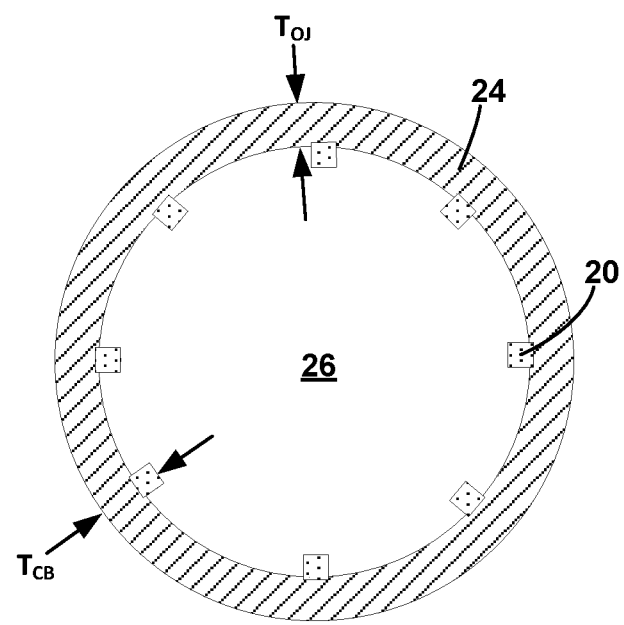
FIG. 10 is a conceptual cross-sectional view of the elongated body of FIG. 2 taken along line C-C in FIG. 2.

FIGS. 8-10 illustrate respective conceptual cross-sectional views of elongated body 12. FIG. 8 is a conceptual cross-sectional view of elongated body 12 of FIG. 1 taken along line A-A of FIG. 2 through a portion of elongated body 12 proximal to expandable member 20. In the example shown in FIG. 8, cross-section A-A of elongated body 12 includes structural support member 28 shown as wire coil, positioned between inner liner 18 and outer jacket 24. The cross-sections shown in FIGS. 8-10 are taken in a direction orthogonal to longitudinal axis 16 (FIG. 1).

FIG. 8 illustrates different thicknesses of elongated body 12 including, a thickness of outer jacket 24 ($T_O$), a thickness of inner liner 18 ($T_{IL}$), and the thickness of elongated body 12 ($T_{CB}$). The total thickness $T_{CB}$ of elongated body 12 may equal to the thickness $T_{IL}$ of inner liner 18 plus the thickness $T_{OJ}$ of outer jacket 24. In some examples, structural support member 28 may also contribute to the total thickness $T_{CB}$ of elongated body 12 and may cause the total thickness $T_{CB}$ to be non-uniform within a given cross-section of elongated body 12. In examples in which elongated body 12 includes a support layer (not shown), the total thickness $T_{CB}$ may likewise include the thickness of the support layer. In other examples, however, structural support member 28 may be embedded in one or both of inner liner 18 or outer jacket 24, and, therefore, may not substantially contribute to the total thickness $T_{CB}$ of elongated body 12. In some examples, the thickness of outer jacket 24 ($T_{OJ}$) may be between about 0.002 inches (about 0.05 millimeters) and about 0.008 inches (about 0.20 millimeters), the thickness of inner liner 18 ($T_{IL}$) may be between about 0.0005 inches (about 0.127 millimeters) and about 0.003 inches (about 0.076 millimeters), and the total thickness $T_{CB}$ of elongated body 12 may be between about 0.003 inches (about 0.076 millimeters) and about 0.010 inches (0.254 millimeters).

FIG. 9 is a conceptual cross-sectional view of elongated body 12 taken along line B-B in FIG. 2, and illustrates an example cross-section of distal portion 17B of elongated body 12 through a proximal portion of expandable member 20. In the example cross-section of FIG. 9, both inner liner 18 and outer jacket 24 extend over a portion of expandable member 20.

FIG. 10 is a conceptual cross-sectional view of elongated body 12 of FIG. 2 taken along line C-C of FIG. 2, and illustrates an example cross-section of distal portion 17B of elongated body 12 through a distal portion of expandable member 20. In the example cross-section of FIG. 10, outer jacket 24 extends over structural expandable member 20 and inner liner 18 is not present. As illustrated in the example of FIG. 10, portions of outer jacket 24 and portions of expandable member 20 may define portions of inner lumen 26.

The catheters described herein may be advanced to a target location within vasculature of the patient in cooperation with a guide wire, retractable sheath, or both, which may aid in the navigation (e.g., steering and manipulation) of the catheter through the vasculature. For example, an inner lumen of the elongated body may be configured to receive a guidewire, such that elongated body 12 may be guided through vasculature over the guidewire.

Figure 11A:
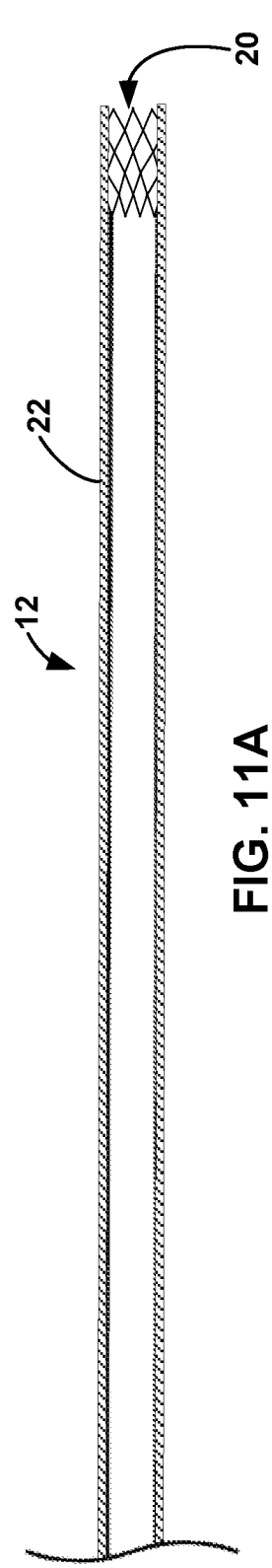
FIGS. 11A and 11B are conceptual cross-sectional side views of an example catheter, which includes a retractable sheath.
Figure 11B:
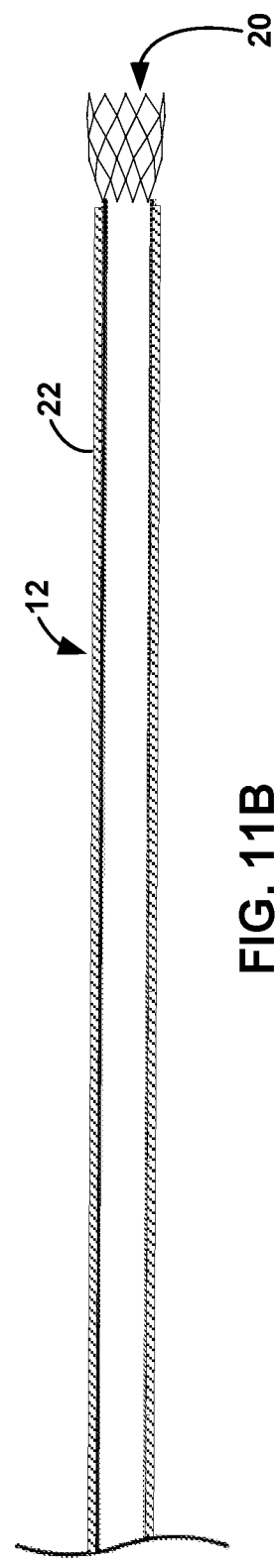

FIGS. 11A and 11B are conceptual cross-sectional side views of expandable member 20 of elongated body 12 being deployed with the aid of a retractable sheath 22. For illustrative purposes, elongated body 12 in FIGS. 11A and 11B includes expandable member 20 however the details of inner liner 18, structural support member 28, and outer jacket 24 are not labeled. FIG. 11A illustrates expandable member 20 in a collapsed configuration within retractable sheath 22 positioned over expandable member 20. Retractable sheath 22 may represent a retractable tubular body on elongated body 12 or may represent the tubular body of a separate delivery catheter. As shown in FIG. 11A, retractable sheath 22 may contain expandable member 20 and prevent the member from self-expanding prior to being positioned adjacent to a target treatment site. Once expandable member 20 is positioned at a desired location, retractable sheath 22 may be withdrawn proximally (e.g., FIG. 11B) to expose expandable member 20, thereby allowing expandable member 20 to expand from the collapsed configuration to an expanded configuration via self-expansion (e.g., construction expandable member 20 with a shape memory metal) or through the aid of an additional device (e.g., expanding expandable member 20 with the aid of a balloon positioned within lumen 26) within vasculature of the patient. Once the aspiration procedure has been completed, retractable sheath 22 may then be extended distally over expandable member 20 to transition expandable member 20 back to the collapsed configuration and catheter 10 may be withdrawn from the patient.

Figure 12:
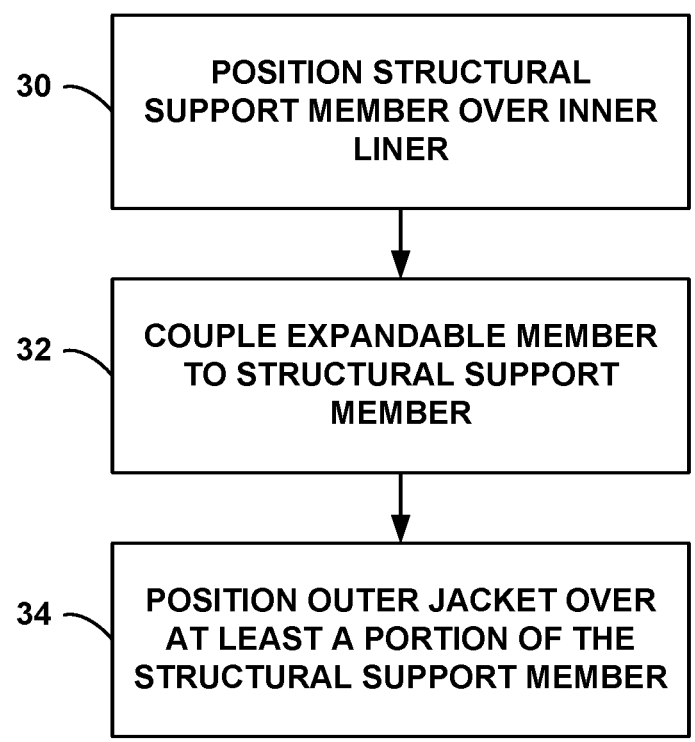
FIG. 12 is a flow diagram of an example method of forming a catheter.
Figure 13:
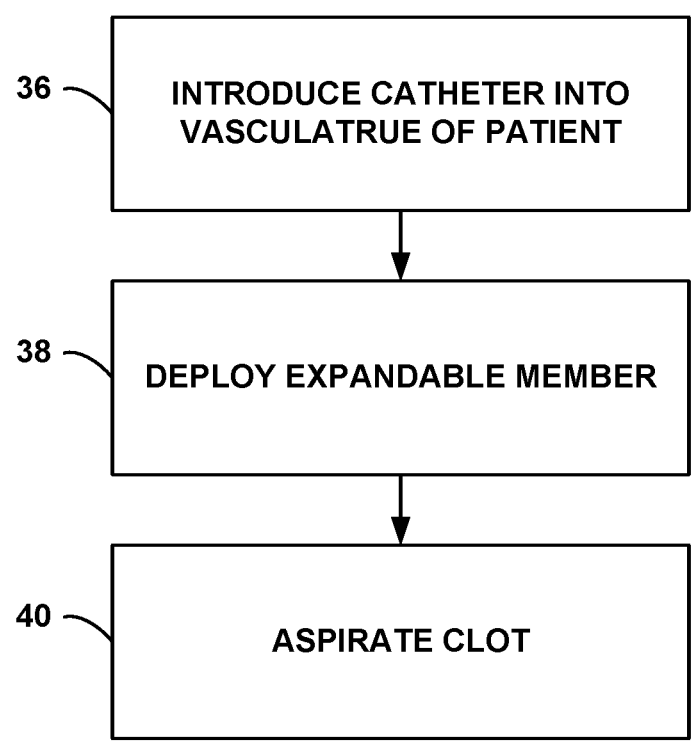
FIG. 13 is a flow diagram of an example method of using a catheter.

FIGS. 12 and 13 describe example techniques for making and using, respectively, the catheters described herein. The techniques of FIGS. 12 and 13 are described with reference to the various aspects of catheter 10 of FIGS. 1 and 2 for illustrative purposes, however, such descriptions are not intended to be limiting and the techniques of FIGS. 12 and 13 may be used to form other catheters, or catheter 10 of FIGS. 1 and 2 may be formed using techniques other than those described in FIG. 12.

FIG. 12 is a flow diagram of an example method of forming catheter 10. The technique of FIG. 12 includes positioning structural support member 28 over inner liner 18 (30); coupling expandable member 20 to structural support member 28 (32); and positioning outer jacket 24 over at least a portion of structural support member 28 (34).

Any suitable device may be used to form inner liner 18. For example, inner liner 18 may be in the form of a tubular body and placed on a mandrel. Inner liner 18 may be fabricated using any suitable technique. In some examples, the respective sections of inner liner 18, where applicable, may be formed using an extrusion process in which the polymeric materials are mechanically mixed together and heated to the melting point of the underlying polymeric material and passed through a tubular extrusion process to form a tubular body having the desire thickness and diameter profiles. In some examples, the respective sections of inner liner 18 (e.g., proximal section 18A and distal section 18B) may be positioned over a mandrel followed by being subsequently joined together (e.g., fused) together. Alternatively, the respective section may be co-extruded to form a unitary tubular body.

In some examples, after positioning inner liner 18 over the mandrel, inner liner 18 may be heat shrunk onto the mandrel such that inner liner 18 conforms to the outer surface of the mandrel and acquire the tapered profile (if applicable) of the mandrel. In such examples, the respective sections of inner liner 18 may be sized such that the inner diameter of the respective liner sections are slightly oversized to facilitate placement of the liner sections on the mandrel prior to the heat shrink process. In other examples, however, heat shrinking may not be necessary. For example, in addition to, or instead of, heat shrinking, the respective sections of inner liner 18 may be longitudinally stretched over the mandrel in order to substantially conform to the outer surface of the mandrel. In either example, inner liner 18 may define a constant inner diameter or may have different inner diameters, e.g., corresponding to the outer diameters defined by the mandrel.

Once inner liner 18 is positioned on the mandrel, structural support member 28 (e.g., a coil, a braid, or combinations thereof) may be positioned over inner liner 18 (30). For example, structural support member 28 may include one or more wire elements (e.g., flat wires, flat-round wires, or round wires) coiled or woven over inner liner 18. Next, expandable member 20 may be positioned over a portion of inner liner 18 and coupled to structural support member 28 (32). For example, where expandable member 20 and structural support member 28 are each formed independently of one another, the proximal end of expandable member 20 may be joined to the distal end of structural support member 28 via welding, brazing, soldering, epoxy, mechanical hooks, or other suitable techniques. In an example, expandable member 20 may not be directly connected to structural support member 28, and may be held in place relative to each other via inner liner 18 and outer jacket 24 (e.g., as shown in FIG. 7).

In other examples, structural support member 28 and expandable member 20 may be integrally formed such that additional coupling is not necessary. For example, catheter 10 may include a hypotube that is cut to form all or a portion of structural support member 28 and expandable member 20 such that the two components are integrally formed from the same hypotube. The hypotube may then be stretched and positioned over inner liner 18. In such examples, the hypotube may be defined to have a diameter less than the outer diameter of inner liner 18. As the hypotube is positioned on inner liner 18, the diameter of the hypotube may be expanded thereby creating a gap between adjacent turns of the hypotube (e.g., the section representing structural support member 28). In other examples, structural support member 28 and expandable member 20 may both be formed using metal wires wherein structural support member 28 and expandable member 20 represent different structures (e.g., coil vs weave) formed by the wires.

In some examples, the structural configuration of structural support member 28 and/or expandable member 20 may be at least partially defined prior to being positioned over inner liner 18. For example, a shape memory wire (e.g., Nitinol alloy) or other structure of an otherwise heat-settable metal, alloy, or polymer base may be formed over a different mandrel where the structure is heat set to define a desired shape of structural support member 28 and/or expandable member 20. After being heat set, structural support member 28 and/or expandable member 20 may then be subsequently removed from the mandrel, and then repositioned over inner liner 18.

In some examples, defining some or all of the structural characteristics of structural support member 28 and/or expandable member 20 prior to positioning the structure over inner liner 18 may help control the structural characteristics of structural support member 28 and/or expandable member 20 (e.g., gap spacings, pitch, expansion characteristics, or the like), as well as control product consistency and uniformity of structural support member 28 and/or expandable member 20 for use in multiple catheters. In addition, shape-setting of the metal structures on a separate, heat-resistant mandrel enables the construction of the elongated body 12 without damaging inner liner 18.

Structural support member 28 and expandable member 20, where applicable, may be secured in place relative to inner liner 18 using any suitable technique. For example, structural support member 28 may be adhered to inner liner 18. In some examples, an adhesive may be positioned over inner liner 18 prior to positioning structural support member 28 over inner liner 18. In addition to, or instead of, an adhesive, outer jacket 24 may be used to secure portions of structural support member 28 and expandable member 20 to inner liner 18.

The technique of FIG. 12 also includes positioning outer jacket 24 over inner liner 18 and structural support member 28 (34). For example, the one or more sections forming outer jacket 24 may be independently formed (e.g., extruded) and slid over inner liner 18, structural support member 28, and expandable member 20 in the desired arrangement. Outer jacket 24 may be connected to inner liner 18 using any suitable technique. For example, outer jacket 24 may be heat shrunk over inner liner 18. A suitable technique for connecting outer jacket 24 to inner liner 18 may include, heating outer jacket 24 while outer jacket 24 is in heat shrink tubing enough to cause the material of outer jacket 24 to melt, then reflow the material of outer jacket 24. In some examples, the heat shrinking of outer jacket 24 may help secure the respective positions of structural support member 28 and/or expandable member 20 along elongated body 12. This may help minimize the wall thickness of elongated body 12 and, therefore, increase the inner diameter of elongated body 12 for a given outer diameter by limiting the inclusion of addition layer within the wall construction of elongated body 12. In addition, the absence of additional layers (e.g., an adhesive/tie/support layer) that joins inner liner 18 to outer jacket 24 may contribute to an increased flexibility of catheter 10. In some examples, during the heat-shrink process, the various sections of outer jacket 24 may also be bonded (e.g., fused) together.

FIG. 13 is a flow diagram of an example method of aspiration using catheter 10. The techniques of FIG. 13 include inserting catheter 10 into vasculature of the patient (36); deploying expandable member 20, which is configured to be expanded in the vasculature of the patient (38); and aspirating a clot (40). In some examples, the techniques described herein include removing catheter 10 from the vasculature of the patient once the procedure is complete. For example, expandable member 20 may be collapsed into a collapsed configuration by advancing retractable sheath 22 distally over expandable member 20, as described further below. In some examples, elongated body 12 may be retracted into a sheath (e.g., sheath 22) to collapse expandable member 20. In some examples, electrical energy may be applied to expandable member 20 to collapse expandable member 20.

In some examples, inserting catheter 10 into vasculature of a patient (36) may be aided by initially introducing a guidewire, guide catheter or another guide member into the vasculature of the patient to a target treatment site. Elongated body 12 may then be introduced over the guidewire and advanced to the target treatment site. Additionally, or alternatively, catheter 10 may be introduced into vasculature of a patient via the aid of a guide catheter. For example, that the guide catheter may be initially introduced into vasculature of a patient and positioned adjacent a target treatment site. Catheter 10 may then be introduced through an inner lumen of the guide catheter.

Once adjacent a target treatment site, expandable member 20 may be deployed into the vasculature (38). In some examples, expandable member 20 may be self-expanding. In such examples, expandable member 20 may be constrained within retractable sheath 22 (e.g., a retractable sheath or the body of a guide catheter) covering expandable member 20. In some examples, expanding expandable member 20 may comprise retracting a sheath (e.g., retractable sheath 22) that may cover expandable member 20 to expose expandable member 20. Once adjacent the target treatment site, retractable sheath 22 may be retracted proximally or otherwise removed from surrounding expandable member 20, thereby allowing expandable member 20 to expand and engage with the vessel wall and/or clot, depending on the location of the expandable member 20 with respect to the clot (or other material to be removed). In some such examples, retractable sheath 22 may form part of catheter 10, or retractable sheath 22 may represent a delivery or guide catheter through which catheter 10 is navigated to reach the target treatment site. In some examples, retractable sheath 22 may be advanced after the suction of the clot is complete, to allow for retraction of expandable member 20 (e.g., re-covering expandable member 20 into the collapsed configuration) and the withdrawal of catheter 10 from the body of the patient.

Additionally, or alternatively, expandable member 20 may be deployed using a balloon to expanded expandable member 20. In examples involving the balloon, the balloon may be navigated through lumen 26 and inflated while within lumen 26 at the distal portion of elongated body 12 to expand expandable member 20. Expandable member 20 may be in the collapsed configuration before expansion (e.g., while within the sheath or before inflating a balloon).

In other examples, expandable member may be expanded by applying electrical energy to expandable member 20. For example, expandable member 20 (or a portion or layer thereof) may be constructed using a shape memory alloy actuator material, as discussed elsewhere herein.

The technique of FIG. 13 also includes initiating aspiration to remove a clot (40). For example, distal end 12B of elongated body 12 may be introduced into an intracranial blood vessel adjacent to and/or proximal of a clot. A vacuum source may be connected to hub 14 and the clot may be suctioned from the blood vessel through inner lumen 26 of elongated body 12 via aspiration. The shape and configuration of expandable member 20 may provide better engagement with the clot. In some examples, distal movement or migration of the clot or other material relative to the expandable member 20 or catheter 10 is prevented or inhibited by the expandable member 20. For example, the inner surface of the expandable member 20 may prevent or inhibit distal movement of the clot/material relative to the expandable member 20 or catheter 10. This may involve entanglement of the clot/material in the expandable member 20, and/or frictional resistance to distal movement of the clot/material by the inner surface of the expandable member 20.

In some examples, electrical energy may be applied to expandable member 20 to better engage the clot. For example, an electrical energy may be delivered to the exposed portions of expandable member 20 via one or more electrical conductors (not shown) coupled to expandable member 20. The electrical energy may be positively charged to electrostatically engage a clot. Characteristics of the electrical energy may be adjusted to better engage the clot, such as polarity, or an amount or type of current delivered. For example, pulsed direct current may be employed, optionally with a non-square and/or non-negative waveform.

Catheter 10 may be removed from the vasculature once the procedure is complete.

Various aspects of the disclosure have been described. These and other aspects are within the scope of the following claims.

What is claimed is:

1. A catheter comprising:
   an elongated body including a proximal portion and a distal portion, the elongated body comprising:
   an inner liner;
   an outer jacket mechanically coupled to the inner liner;
   a structural support member positioned between at least a portion of the inner liner and at least a portion of the outer jacket; and
   an expandable member mechanically coupled to the structural support member at the distal portion of the elongated body, wherein the expandable member is configured to expand radially outward from a collapsed configuration to an expanded configuration, wherein the expandable member comprises a plurality of struts defining a plurality of cells, and wherein the outer jacket extends over at least a portion of the expandable member that expands radially outward when the expandable member is in the expanded configuration and when the expandable member is in the collapsed configuration.

2. The catheter of claim 1, wherein the expandable member is mechanically coupled to the structural support member at a plurality of circumferential positions of the structural support member.

3. The catheter of claim 2, wherein proximal peaks of at least one strut of the plurality of struts are coupled to the structural support member.

4. The catheter of claim 1, wherein the expandable member is configured to engage a clot.

5. The catheter of claim 4, wherein an inner surface of the expandable member comprises a surface treatment configured to promote at least one of mechanical or chemical engagement between the inner surface and the clot.

6. The catheter of claim 5, wherein the surface treatment comprises at least one of surface etching, a positive electrical charge, or a cationic polymer.

7. The catheter of claim 1, wherein a proximal end of the expandable member is at least one of positioned over at least a portion of the inner liner, or positioned under at least a portion of the outer jacket.

8. The catheter of claim 7, wherein the inner liner comprises a first section and a second section distal to the first section, the structural support member positioned over the first section and the expandable member positioned over the second section, and wherein the second section of the inner liner has a lower modulus of elasticity than the first section.

9. The catheter of claim 7, wherein the inner liner comprises a first section and a second section distal to the first section, the structural support member positioned over the first section and the expandable member positioned over the second section, and wherein the second section of the inner liner has a lower coefficient of friction than the first section.

10. The catheter of claim 7, wherein the inner liner comprises a first section and a second section distal to the first section, the structural support member positioned over the first section and the expandable member positioned over the second section, and wherein the second section of the inner liner is configured to have a higher affinity to a clot than the first section of the inner liner.

11. The catheter of claim 7, wherein the inner liner comprises a first section and a second section distal to the first section, the structural support member positioned over the first section and the expandable member positioned over the second section, and wherein an inner surface of the second section is configured to promote at least one of mechanical or chemical clot engagement.

12. The catheter of claim 11, wherein the inner surface of the second section of the inner liner is etched to promote mechanical clot engagement.

13. The catheter of claim 1, wherein the elongated body comprises an electrical conductor electrically coupled to the expandable member, the expandable member configured to receive an electrical signal via the electrical conductor that causes the expandable member to electrostatically engage a clot.

14. The catheter of claim 13, wherein the expandable member is configured to expand radially outward in response to receiving the electrical signal.

15. The catheter of claim 1, wherein the outer jacket is heat shrunk over the inner liner.

16. The catheter of claim 1, wherein the structural support member defines inner spacings or gaps, and wherein portions of the outer jacket are positioned in the inner spacings or the gaps.

17. The catheter of claim 1, further comprising a sheath configured to retain the expandable member in the collapsed configuration, wherein the expandable member and the outer jacket are configured to expand radially outward when the sheath is withdrawn proximally to expose the expandable member.

18. The catheter of claim 1, wherein at least a distal portion of the outer jacket that extends over the expandable member is configured to flexibly accommodate radial expansion of the expandable member from the collapsed configuration to the expanded configuration.

19. A catheter comprising:
   an elongated body comprising:
   an inner liner;
   an outer jacket mechanically coupled to the inner liner;
   a structural support member; and
   an expandable member distal to the structural support member, wherein the structural support member and at least a portion of the expandable member are positioned between the inner liner and the outer jacket, wherein the expandable member comprises a plurality of struts defining a plurality of cells, and wherein the outer jacket extends over at least a portion of the expandable member that expands radially outward when the expandable member is expanded radially outward in an expanded configuration and when the expandable member is in a collapsed configuration.

20. The catheter of claim 19, wherein the expandable member is mechanically coupled to the structural support member at a plurality of circumferential positions of the structural support member.

21. The catheter of claim 20, wherein proximal peaks of the plurality of struts are coupled to the structural support member.

22. The catheter of claim 19, wherein the expandable member is configured to engage a clot.

23. The catheter of claim 22, wherein an inner surface of the expandable member comprises a surface treatment configured to promote at least one of mechanical or chemical engagement between the inner surface and the clot.

24. The catheter of claim 23, wherein the surface treatment comprises at least one of surface etching, a positive electrical charge, or a cationic polymer.

25. The catheter of claim 19, wherein a proximal end of the expandable member is at least one of positioned over at least a portion of the inner liner, or positioned under at least a portion of the outer jacket.

26. The catheter of claim 25, wherein the inner liner comprises a first section and a second section distal to the first section, the structural support member positioned over the first section and the expandable member positioned over the second section, and wherein the second section of the inner liner has a lower modulus of elasticity than the first section.

27. The catheter of claim 25, wherein the inner liner comprises a first section and a second section distal to the first section, the structural support member positioned over the first section and the expandable member positioned over the second section, and wherein the second section of the inner liner has a lower coefficient of friction than the first section.

28. The catheter of claim 25, wherein the inner liner comprises a first section and a second section distal to the first section, the structural support member positioned over the first section and the expandable member positioned over the second section, and wherein the second section of the inner liner is configured to have a higher affinity to a clot than the first section of the inner liner.

29. The catheter of claim 25, wherein the inner liner comprises a first section and a second section distal to the first section, the structural support member positioned over the first section and the expandable member positioned over the second section, and wherein an inner surface of the second section is configured to promote at least one of mechanical or chemical clot engagement.

30. The catheter of claim 29, wherein the inner surface of the second section of the inner liner is etched to promote mechanical clot engagement.

* * * * *